US010845355B2

United States Patent
Koseoglu

(10) Patent No.: US 10,845,355 B2
(45) Date of Patent: Nov. 24, 2020

(54) CHARACTERIZATION OF CRUDE OIL BY FOURIER TRANSFORM NEAR INFRARED SPECTROMETRY

(71) Applicants: Saudi Arabian Oil Company, Dhahran (SA); Omer Refa Koseoglu, Dhahran (SA)

(72) Inventor: Omer Refa Koseoglu, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 453 days.

(21) Appl. No.: 15/541,206

(22) PCT Filed: Jan. 5, 2016

(86) PCT No.: PCT/US2016/012160
§ 371 (c)(1),
(2) Date: Jun. 30, 2017

(87) PCT Pub. No.: WO2016/111997
PCT Pub. Date: Jul. 14, 2016

(65) Prior Publication Data
US 2017/0370897 A1 Dec. 28, 2017

Related U.S. Application Data

(60) Provisional application No. 62/099,788, filed on Jan. 5, 2015.

(51) Int. Cl.
*G01N 33/28* (2006.01)
*G06Q 30/02* (2012.01)
*G01N 30/88* (2006.01)

(52) U.S. Cl.
CPC ..... *G01N 33/2835* (2013.01); *G01N 33/2823* (2013.01); *G06Q 30/0283* (2013.01);
(Continued)

(58) Field of Classification Search
CPC ........... G01N 33/2835; G01N 33/2823; G01N 2030/8854; G06Q 30/0283;
(Continued)

(56) References Cited

U.S. PATENT DOCUMENTS 3,617,501 A * 11/1971 Eng .................. C10G 47/00
208/89
3,896,312 A * 7/1975 Brown ............... G01N 21/3577
250/343

(Continued)

FOREIGN PATENT DOCUMENTS

CA 2781273 A1 12/2013
EP 0305090 A2 8/1988
(Continued)

OTHER PUBLICATIONS

Adhvaryu, A. et al., Quantitative NMR Spectroscopy for the Prediction of Base Oil Properties, Tribology Transactions, vol. 43, No. 2, 2000, pp. 245-250.
(Continued)

*Primary Examiner* — Mohammad K Islam
(74) *Attorney, Agent, or Firm* — Abelman, Frayne and Schwab

(57) ABSTRACT

A system and a method for determining the aromatic content and naphthene content of a naphtha fraction of a stream is provided, by conducting analysis on the crude oil sample. Crude oil analysis data is obtained from the sample, and modules or steps are performed to calculate an index. The index is used to assign aromatic content and naphthene content to the crude oil sample.

12 Claims, 3 Drawing Sheets

(52) U.S. Cl.
CPC .............. *C10G 2300/104* (2013.01); *C10G 2300/1044* (2013.01); *C10G 2300/305* (2013.01); *C10G 2300/308* (2013.01); *G01N 2030/8854* (2013.01)

(58) Field of Classification Search
CPC ...... C10G 2300/308; C10G 2300/1044; C10G 2300/104; C10G 2300/305
See application file for complete search history.

(56) References Cited

U.S. PATENT DOCUMENTS

| | | | |
|---|---|---|---|
| 4,251,870 A * | 2/1981 | Jaffe | G01N 33/2829 700/268 |
| 4,897,177 A * | 1/1990 | Nadler | C10G 35/095 208/135 |
| 4,971,915 A * | 11/1990 | Schwartz | G01N 25/08 436/139 |
| 4,988,446 A * | 1/1991 | Haberman | C10G 11/187 210/198.2 |
| 5,121,337 A * | 6/1992 | Brown | G01N 21/274 250/339.12 |
| 5,145,785 A * | 9/1992 | Maggard | G01N 21/359 250/252.1 |
| 5,223,714 A * | 6/1993 | Maggard | G01N 21/359 250/339.12 |
| 5,266,800 A * | 11/1993 | Mullins | G01N 21/359 250/253 |
| 5,304,807 A | 4/1994 | Lin | |
| 5,362,965 A * | 11/1994 | Maggard | G01N 21/359 250/339.12 |
| 5,424,959 A | 6/1995 | Reyes | |
| 5,452,232 A * | 9/1995 | Espinosa | G01N 21/3577 702/30 |
| 5,475,612 A | 12/1995 | Espinosa | |
| 5,490,085 A | 2/1996 | Lambert et al. | |
| 5,572,030 A | 11/1996 | Ranson et al. | |
| 5,600,134 A | 2/1997 | Ashe et al. | |
| 5,602,755 A | 2/1997 | Ashe et al. | |
| 5,656,810 A | 8/1997 | Alfano et al. | |
| 5,699,269 A | 12/1997 | Ashe et al. | |
| 5,699,270 A | 12/1997 | Ashe et al. | |
| 6,070,128 A | 5/2000 | Descales | |
| 6,258,987 B1 | 7/2001 | Schmidt et al. | |
| 6,275,775 B1 | 8/2001 | Baco | |
| 6,490,029 B1 | 12/2002 | Cho | |
| 6,602,403 B1 | 8/2003 | Steffens et al. | |
| 6,611,735 B1 | 8/2003 | Henly | |
| 6,633,043 B2 | 10/2003 | Hegazi | |
| 6,662,116 B2 | 12/2003 | Brown | |
| 6,711,532 B1 | 3/2004 | Spieksma | |
| 6,841,779 B1 * | 1/2005 | Roehner | G01N 33/2811 250/339.06 |
| 6,893,874 B2 | 5/2005 | Stark | |
| 7,126,332 B2 | 10/2006 | Blanz | |
| 7,173,239 B2 | 2/2007 | DiFoggio | |
| 7,560,711 B2 | 7/2009 | Hegazi | |
| 7,598,487 B2 | 10/2009 | Qian | |
| 8,714,246 B2 | 5/2014 | Pop et al. | |
| 8,930,149 B1 | 1/2015 | Koseoglu et al. | |
| 9,285,307 B2 | 3/2016 | Koseoglu et al. | |
| 9,423,391 B2 | 8/2016 | Koseoglu et al. | |
| 9,428,697 B2 * | 8/2016 | Zhou | C10G 7/00 |
| 9,429,556 B2 | 8/2016 | Koseoglu et al. | |
| 9,453,830 B2 * | 9/2016 | Zhang | G01N 30/7206 |
| 9,745,198 B2 * | 8/2017 | Leventis | C01B 32/97 |
| 9,778,240 B2 | 10/2017 | Koseoglu et al. | |
| 9,816,919 B2 | 11/2017 | Koseoglu et al. | |
| 9,969,943 B2 * | 5/2018 | Bennetzen | C10G 25/003 |
| 2002/0052769 A1 | 5/2002 | Navani et al. | |
| 2002/0062796 A1 * | 5/2002 | Thieleke | B25C 1/08 123/46 SC |
| 2003/0141459 A1 | 7/2003 | Hegazi et al. | |
| 2003/0195708 A1 * | 10/2003 | Brown | G01N 21/35 702/22 |
| 2004/0069942 A1 * | 4/2004 | Fujisawa | G01N 21/359 250/269.1 |
| 2005/0109934 A1 | 5/2005 | David | |
| 2005/0173298 A1 | 8/2005 | Wellington | |
| 2006/0043004 A1 | 3/2006 | Rose | |
| 2006/0047444 A1 * | 3/2006 | Brown | G01N 33/2823 702/30 |
| 2006/0142955 A1 | 6/2006 | Jones | |
| 2007/0050154 A1 | 3/2007 | Albahri | |
| 2007/0231912 A1 | 10/2007 | Reischman et al. | |
| 2007/0295640 A1 | 12/2007 | Tan et al. | |
| 2008/0037006 A1 | 2/2008 | Canas Triana | |
| 2008/0040051 A1 | 2/2008 | Franklin et al. | |
| 2008/0206887 A1 | 8/2008 | Chen | |
| 2008/0248967 A1 | 10/2008 | Butler et al. | |
| 2008/0253426 A1 | 10/2008 | Voelkening | |
| 2008/0260584 A1 | 10/2008 | Gudde et al. | |
| 2009/0011517 A1 | 1/2009 | Hodges | |
| 2009/0180949 A1 | 7/2009 | Cui | |
| 2009/0279072 A1 | 11/2009 | Arakawa | |
| 2009/0290144 A1 | 11/2009 | Hegazi | |
| 2009/0316139 A1 | 12/2009 | Shrestha | |
| 2010/0049681 A1 | 2/2010 | Pradhan | |
| 2010/0113311 A1 | 5/2010 | Eccleston et al. | |
| 2010/0204925 A1 * | 8/2010 | Albahri | G01N 25/14 702/25 |
| 2010/0211329 A1 | 8/2010 | Farquharson et al. | |
| 2010/0218585 A1 | 9/2010 | Chawla | |
| 2011/0152136 A1 | 6/2011 | Hughes et al. | |
| 2011/0308996 A1 | 12/2011 | Choudhary | |
| 2012/0171151 A1 | 7/2012 | Thomassian | |
| 2013/0016336 A1 * | 1/2013 | Xie | G01N 21/359 356/51 |
| 2014/0075827 A1 | 3/2014 | Gonzalez et al. | |
| 2014/0156241 A1 | 6/2014 | Kumar et al. | |
| 2015/0106027 A1 | 4/2015 | Koseoglu et al. | |
| 2015/0106028 A1 | 4/2015 | Koseoglu et al. | |
| 2015/0106029 A1 | 4/2015 | Koseoglu et al. | |
| 2015/0106031 A1 | 4/2015 | Koseoglu et al. | |
| 2015/0112610 A1 | 4/2015 | Koseoglu | |
| 2015/0112611 A1 | 4/2015 | Koseoglu | |
| 2015/0167456 A1 * | 6/2015 | Irani | E21B 47/113 73/152.23 |
| 2016/0011102 A1 | 1/2016 | Koseoglu et al. | |
| 2016/0187253 A1 | 6/2016 | Koseoglu et al. | |
| 2016/0195481 A1 | 7/2016 | Koseoglu | |
| 2016/0195507 A1 | 7/2016 | Koseoglu | |
| 2016/0195508 A1 | 7/2016 | Al-Hajji | |
| 2016/0377589 A1 | 12/2016 | Koseoglu | |
| 2017/0003217 A1 | 1/2017 | Koseoglu | |
| 2017/0363540 A1 | 12/2017 | Koseoglu | |
| 2017/0363591 A1 | 12/2017 | Koseoglu | |
| 2017/0363602 A1 | 12/2017 | Koseoglu | |
| 2017/0363603 A1 | 12/2017 | Koseoglu | |

FOREIGN PATENT DOCUMENTS

| | | |
|---|---|---|
| EP | 0304232 A2 | 2/1989 |
| EP | 0552300 A1 | 7/1993 |
| EP | 0794433 A1 | 9/1997 |
| EP | 0859236 A1 | 8/1998 |
| EP | 0984277 A1 | 3/2000 |
| SU | 817486 A1 | 3/1981 |
| SU | 1523972 A1 | 11/1989 |
| WO | 03/048759 A1 | 6/2003 |
| WO | 2004033513 A1 | 4/2004 |
| WO | 2006030218 A1 | 3/2006 |
| WO | 2009082418 A2 | 7/2009 |
| WO | 2013102916 A1 | 7/2013 |

OTHER PUBLICATIONS

Albahri, T. et al, Octane Number and Aniline Point of Petroleum Fuels, 2002, Fuel Chemistry Division, vol. 47(2), pp. 710-711.

(56) References Cited

OTHER PUBLICATIONS

Ali, M., Resolution and Quantification of Ring Type Aromatics by HPLC Method using N-Hexane Elution, 2003, King Fahd University of Petroleum and Minerals, pp. 1-9.
ASTM D2887-01, Standard Test Method for Boiling Range Distribution of Petroleum Fractions by Gas Chromatography, Annual Book of ASTM Standards, vol. 14, No. 02, pp. 204-216.
Birch C., Oil & Gas Journal, Jan. 14, 2002, pp. 54-59 (printed Jul. 9, 2014 from http://www.ogj.com/articles/print/volume-100/issue-2/processing/achieving-maximum-crude-oil-value-depends-on-accurate-evaluation.html).
Bowden, J. et al., Octane-Cetane Relationship, 1974, NTIS, p. 8.
Chemstations, Inc., Physical Properties Users Guide, 2004, Chemstations Inc., Ver. 5.4, pp. 18-22.
Cookson, D.J. et al., Investigation of the Chemical Basis of Diesel Fuel Properties, Energy & Fuels, vol. 2, No. 6, 1988, pp. 854-860.
Duvekot, C., Fast Analysis of Paraffins, iso-Paraffins, Olefins, iso-Olefins, Naphthenes and Aromatics in Hydrocarbon Streams, Varian, Inc., 2008, pp. 1-4.
Evokimov, I, et al, Potential of UV-Visible Absorption Spectroscopy for characterizing Crude Petroleum Oils, Oil an Gas Business, 2007, 21 pages.
Falla, F, et al., Characterization of crude petroleum by NIR, Journal of Petroleum Science and Engineering, vol. 51, 2006, pp. 127-137.
Fernandez-Lima, F. et al., Petroleum Crude Oil Characterization by IMS-MS and FTICR MS, 2009, American Chemical Society, Ed. 81, pp. 9941-9945.
Grizzle, P. et al., Automated Liquid Chromatographic Compound Class Group-Type Separation of Crude Oils and Bitumens Using Chemically Bonded Aminolilane, 1986, Publisher Anal. Chem., vol. 58, pp. 2389-2390.
Hasan, M.U. et al., Structural characterization of Saudi Arabian heavy crude oil by n.m.r. spectroscopy, Fuel, vol. 62, 1983, pp. 518-523.
Hidajat, K, et al., Quality characterisation of crude oils by partial least square calibration of NIR spectral profiles, Near Infrared Spectrosc, vol. 8, pp. 53-59, 2000.
Jokuty, P. et al., Hydrocarbon Groups and Their Relationships to Oil Properties and Behavior, 1995, Published by Whiticar Scientific, p. 11.
Khanmohammadi, M, et al., Characterization of petroleum-based products by infrared spectroscopyu and chemometrics, Trac Trends in Analytical Chem, vol. 35, 2012.
Kok, M, et al., High pressure TGA analysis of crude oils, Thermochimica Acta., vol. 287, No. 1, 1996, pp. 91-99.
Mckenna, Amy M., Heavy Petroleum Composition. 1. Exhaustive Compositional Analysis of Athabasca Bitumen HVGO Distillates by Fourier Transform Ion Cyclotron Resonance Mass Spectrometry: A Definitive Test of the Boduszynski Model, Energy Fuels, 24, 2010, pp. 2929-2038.
Mohammed, S., The Use of Compounds Chemically Related to Analyte as Surrogate Reference Standards in Quantitative HPLC, Feb. 2008, Produced by Kwame Nkrumah University of Science and Technology, Kumasi, p. 16.
Pande, S., et al., Cetana Number Predictions of a Trial Index Based on Compositional Analysis, American Chemical Society, 1989, pp. 308-312.
Patra, D, et al, Determination of Synchronous Fluorescence Scan Parameters for Certain Petroleum Products, Journal of Scientific & Industrial Research, Apr. 1, 2000, pp. 300-305.
Pavlovic K., Oil & Gas Journal, Nov. 22, 1999, pp. 51-56 (printed Jul. 9, 2014 from http://www.ogj.com/articles/print/volume-97/issue-47/in-this-issue/refining/gravity-and-sulfur-based-crude-valuations-more-accurate-than-believed.html).
Pereira,Thieres M. C., An evaluation of the aromaticity of asphaltenes using atmospheric pressure photoionization Fourier transform ion cyclotron resonance mass spectrometry—APP (±) FT-ICR MS, Fuel, 2014, vol. 118, 2014, pp. 348-357.
Rodgers, R. et al., Advanced Characterization of Petroleum Crude and Products by High Field Fourier Transform Ion cyclotron Resonance Mass Spectrometry, 2002, Fuel Chemistry Division, Ed. 47(2), pp. 636-637.
Shea, T.M., Modeling Base Oil Properties using NMR Spectroscopy and Neural Networks, Tribology Transactions, vol. 46, No. 3, 2003, pp. 296-302.
Souza, C. et al., Cetane Number Assessment in Diesel Fuel by 1H or Hydrogen Nuclear Magnetic Resonance-Based Multivariate Calibration, Energy & Fuels, vol. 28, 2014, pp. 4958-4962.
Speight, Handbook of Petroleum Product Analysis, 2002.
Terra, L. et al., Petroleomics by electrospray ionization FT-ICR mass spectrometry coupled to partial least squares with variable selection methods: prediction of the total acid number of crude oils, 2014, Analyst, vol. 139, 2014, pp. 4908-4916.
University of Oldenburg, Institute of Physics, Catalogue of Optical Spectra of Oils, Jan. 2005, retrieved from http://las.physik.uni-oldenburg.de/data/spectra/indez.htm, 6 pages.
Yamashita, G.T., Evaluation of Integration Procedures for PNA Analysis by C-13 NMR, Symposium on Analytical Chemistry of Heavy Oils/Resids Presented Before the Division of Petroleum Chemistry, Inc., American Chemical Society, Dallas Meeting, Apr. 9-14, 1989, pp. 301-305.
PCT/US2016/012160, International Search Report and Written Opinion dated May 2, 2016, 12 pages.

\* cited by examiner

CHARACTERIZATION OF CRUDE OIL BY FOURIER TRANSFORM NEAR INFRARED SPECTROMETRY

RELATED APPLICATIONS

This application claims the benefit of U.S. Provisional Patent Application No. 62/099,788 filed Jan. 5, 2015, the disclosure of which is hereby incorporated by reference.

FIELD OF THE INVENTION

This invention relates to a method and process for the valuation of samples of crude oil and its fractions.

BACKGROUND OF THE INVENTION

There are more than 200 crude oils produced and traded worldwide. Crude oils are very complex mixtures of many thousands of different hydrocarbons. Depending on the source, the oils contain various proportions of straight and branched-chain paraffins, cycloparaffins, and naphthenic, aromatic and polynuclear aromatic hydrocarbons. The nature of the crude oil governs, to a certain extent, the nature of the products that can be manufactured from it and their suitability for specific applications.

Worldwide supply and demand, regional refining capacities and configurations, and crude composition are the key factors that determine the value of crude oil. The first factor is purely market-dependent and cannot be predicted from the crude oil quality. Accordingly, the crude oil value is determined by the regional crude market and differentials such as freight, quality adjustments, refining cost and competitive pricing.

In a typical petroleum refinery, crude oil is first distilled under atmospheric pressure. Gases will rise to the top of the distillation column, followed by lower boiling liquids, including, naphtha, kerosene and diesel oil. Naphtha is not a final product, but is subjected to additional treatment steps, such as hydrotreating and catalytic reforming to produce reformate. The reformate is then sent to a gasoline pool for blending.

An article by Colin Birch, "Achieving Maximum Crude Oil Values Depends on Accurate Evaluation," Oil & Gas Journal, Vol. 100, Issue 2 (Jan. 14, 2002), describes a number of evaluation methods for obtaining an objective calculation of the value of a specific crude oil from a particular source. Summaries of several of these methods follow.

Bulk-Property Method: This method correlates actual crude value with bulk properties. API gravity and sulfur content are widely used for the correlation, and other bulk properties, such as viscosity and pour point, can also be used. This method is relatively simple in terms of the amount of testing required. However, this method may not be reliable when a large range of crudes are being valued. For example, some of the naphthenic crudes may be valued relatively higher, using this method, but this result may not reflect the actual market value for the crude oil.

Refining-Value Method: Crude oils are evaluated and valued using the refinery yields and process operating costs for each crude stream, typically using a linear program (LP) or other model. Refinery models require detailed physical property information and distillation cuts as determined by a detailed crude oil assay. Process yields and operating costs are used with appropriate product values to calculate refining-value differentials between the crude oils. The refining-value method simulates the process used by refiners for selecting crude oils. Detailed crude oil quality information and the need to run a refinery model for a given refinery to generate the yields make this method more complex than the bulk-property method. If input stream quality changes significantly, a new set of yields must be generated. In relatively simple systems involving only a few crudes with reasonably stable quality, the refining-value method normally provides the most accurate value allocation for a refiner.

Distillation-Yield Method: This is a simplified version of the refining-value method, which instead of using a linear program or other model will only use the yield of each fraction. These product yields from distilling each crude are used with product values to calculate the relative value of each crude. In many cases, some physical properties of the distillation cuts are used in the value-adjustment system. The quality information from each crude is relatively simple and includes distillation yields and distillation cut properties. The distillation yield-method is more complex than the bulk-property method, but less complex than the refining-value method. Because it uses product values in the calculation, reliability of crude oil value data is not an issue. The products being valued, however, such as naphtha, are not finished products meeting defined specifications. So there is some uncertainty regarding the value adjustment for key properties of the distillation cuts.

Several properties of naphtha streams can be evaluated, including API gravity, sulfur, nitrogen, carbon and hydrogen contents, and research octane number. Research octane number is the measure of a fuel's ability to prevent detonation in a spark-ignition engine. Measured in a standard single-cylinder, variable-compression-ratio engine by comparison with primary reference fuels, American Standard Testing Material Tests ASTM D-2699 and ASTM D-2700 describe the determination of research and motor octane numbers, respectively. Under mild conditions, the engine measures research octane number (RON), while under sever conditions the engine measures motor octane number (MON). Where the law requires posting of octane numbers on dispensing pumps, the antiknock index (AKI) is used. This is the arithmetic average of RON and MON, namely, (R+M)/2. It approximates the road octane number, which is a measure of how an "average" car responds to fuel. It is the most critical property for naphtha/gasoline streams.

The RON of a spark-ignition engine fuel is determined using a standard test engine and operating conditions to compare its knock characteristic, defined as knock intensity (KI) with those of primary reference fuel (PRF) blends (containing iso-octane and normal heptane) of known octane number. For example, an 87-octane gasoline has the same octane rating as a mixture of 87% iso-octane and 13% n-heptane. Compression ratio (CR) and fuel-air ratio are adjusted to produce standard KI for the sample fuel, as measured by a specific electronic detonation meter instrument system. A standard KI guide table relates engine CR to octane number level for this specific method. The fuel-air ratio for the sample fuel and each of the primary reference fuel blends is adjusted to maximize KI for each fuel. While gasoline will have an RON of 85 or higher, naphtha will have an RON below 60.

The MON of a spark-ignition engine fuel is determined using a standard test engine and operating conditions to compare its knock characteristic with those of PRF blends of known octane number. CR and fuel-air ratios are adjusted to produce standard KI for the sample fuel, as measured by a specific electronic detonation meter instrument system. A standard KI guide table relates engine CR to octane number level for this specific method. The fuel-air ratio for the sample fuel and each of the PRF blends is adjusted to maximize KI for each fuel.

To determine these properties of gas oil or naphtha fractions conventionally, these fractions have to be distilled from the crude oil and then measured/identified using various analytical methods that are laborious, costly and time-consuming.

Therefore, a need exists for an improved system and method for determining the value of crude oils from different sources that can be objectively applied to compare the naphtha fractions from different sources.

SUMMARY OF THE INVENTION

Systems and methods for assigning a value to a naphtha stream are provided. The stream is reformed to a target research octane number, and plural light component fractions and a reformate fraction are obtained; the reformate fraction is analyzed to obtain data indicative of the content naphthenes and aromatics, and in certain embodiments additionally paraffins and iso-paraffins, and in further embodiments additionally paraffins, iso-paraffins olefins, and iso-olefins. The indicative data is used to assign a feed quality. The assigned feed quality is used to assign a total liquid yield and raw products yields, which are individually assigned values. A total naphtha valuation can thus be assigned based on the indicative data. When the method is applied to naphtha streams derived from crude oils from various sources, the respective assigned values provide an objective basis for relative evaluation of the crude oil.

The system and method of the invention can be utilized to valuate naphtha fractions derived from crude oils, which fractions have nominal boiling points in the range of −11.5 to 235° C., and in certain embodiments from 36-180° C. Naphtha fractions vary in composition and, as a result, octane number, which, as discussed above, is a key indicative property for engine-knocking characteristic. The difference in composition and properties make the evaluation of the naphtha fraction difficult. In a certain embodiments, the comparative evaluation method disclosed herein is practiced on straight run naphtha samples.

In certain embodiments of the method herein, the naphtha fraction is converted to light components and a reformate of a target research octane number in a catalytic reforming process. The reformate is fed into a gas chromatograph to obtain data indicative of the content naphthenes and aromatics, and in certain embodiments additionally paraffins and iso-paraffins, and in further embodiments additionally paraffins, iso-paraffins olefins, and iso-olefins, e.g., known as a PIONA analysis. An algorithm is applied to the total percentages of the naphthenes and aromatics in order to determine a value of the naphtha stream. The value of each of the components is assigned based upon independently determined values at a given time and place that is predetermined by the user.

In further embodiments of the methods and systems herein, the content of naphthenes and aromatics in the naphtha fraction is assigned as a function of the density of a crude oil sample and an index derived from analysis of the crude oil sample. The analysis is selected from any one of Fourier transform near infrared spectroscopy, Fourier transform infrared spectroscopy, Fourier transform ion cyclotron mass spectroscopy, time of flight mass spectroscopy, ultraviolet visible spectroscopy, laser induced ultraviolet spectroscopy, nuclear magnetic spectroscopy, fluorescence spectroscopy, Raman spectroscopy, gas chromatography, liquid chromatography, supercritical fluid chromatography, thermogravimetric analysis, or differential scanning calorimetry.

The methods and systems herein can be applied to samples derived from different crude oils obtained from different reservoirs or regions to provide relative values for the same RON in order to provide refiners with a basis for comparison in the market(s) in which their products are sold. Accordingly, an object of the method and system herein is to facilitate comparison of two or more streams in order to ascertain which stream has a higher value based upon the current value for its constituent fractions. Such data is useful, for instance, to provide the refiner with a basis for deciding which stream should be processed first.

Another object of this invention is to provide a method for evaluation of particular naphtha streams derived from crude oils from various sources to establish an objective basis for economic comparison based on specific value.

In the description herein, the terms "reformer unit", "reformer" and "reforming unit" are used interchangeably, and refer to conventional apparatus used in a catalytic reforming process.

BRIEF DESCRIPTION OF THE DRAWINGS

Further advantages and features of the present invention will become apparent from the following detailed description of the invention when considered with reference to the accompanying drawing, in which.

DETAILED DESCRIPTION OF INVENTION

A system and method is provided for determining and assigning yields and valuation of a hydrocarbon sample. Reformate component yields of a naptha fraction derived in certain embodiments from crude oil samples are assigned as a function of the PIONA analysis data of a crude oil sample. The correlations also provide information about naphtha component and total yields without fractionation/distillation (crude oil assays) and enables producers, refiners, and marketers to benchmark the oil quality and, as a result, valuate the oils without performing the customary extensive and time-consuming crude oil assays.

The systems and methods are applicable for evaluation of naphtha streams derived from crude oils, bitumens, heavy oils, shale oils and from refinery process units including hydrotreating, hydroprocessing, fluid catalytic cracking, coking, and visbreaking or coal liquefaction.

Figure 1:
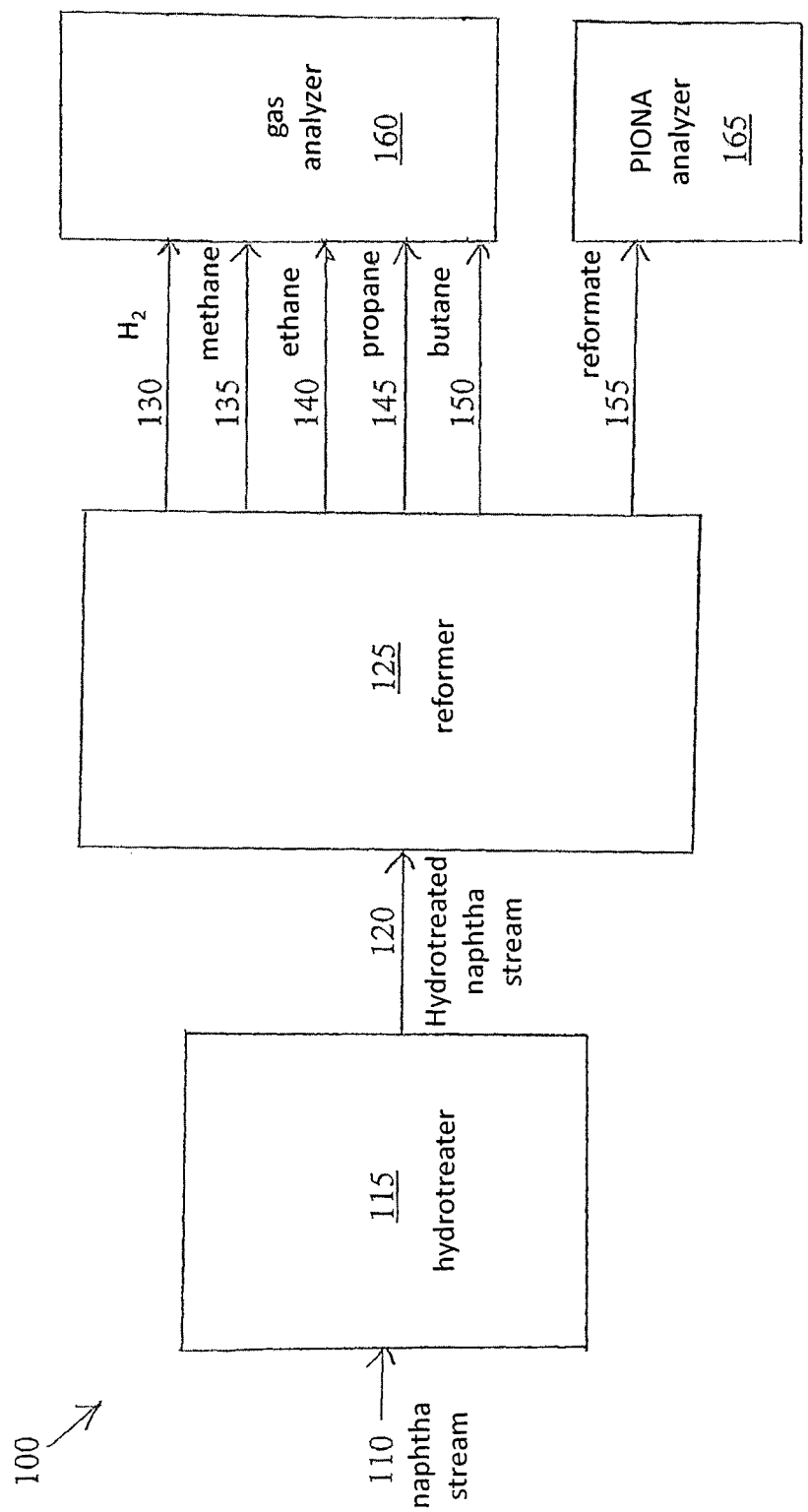
FIG. 1 schematically illustrates the hydrotreating and reformation of naphtha and the chromatograph analysis of the resultant streams.

FIG. 1 shows the hydrotreating and reforming process 100. Naphtha stream 110 is fed into a hydrotreater 115 to produce a hydrotreated naphtha stream 120, which is passed to a reformer 125. Light component streams hydrogen ("H2") 130, methane ("C1") 135, ethane ("C2") 140, propane ("C3") 145, and butane ("C4") 150, and reformate ("C5+") 155, are recovered from reformer 125. Operating conditions are such that the reformate is characterized by a target research octane number. Thus, while the product yield distribution will differ for each naphtha feedstock produced, the quality of gasoline, as measured by the research octane number, will be uniform.

The predetermined research octane number selected can be in the range of from 80 to 100 for products coming from the reforming unit, in certain embodiments in the range of from 95 to 100, and in further embodiments in the range of from 95 to 98, which is the gasoline RON specification. It is to be noted that the yield typically declines with an increase in the target octane number.

In certain embodiments, hydrotreater 115 operates under conditions and in the presence of one or more catalysts effective to produce a hydrotreated naphtha stream 120 having sulfur levels below 0.5 ppmw and nitrogen levels below 0.5 ppmw. The maximum allowable sulfur and nitrogen contaminant content levels should be maintained within the predetermined limits established for efficient use of the reformer unit catalyst. The reformer catalyst is made of noble metals such as platinum and palladium and is very sensitive to impurities like sulfur and nitrogen. The presence of higher levels of sulfur and nitrogen during the operation will poison the catalyst. As is known to those of ordinary skill in the art, the major sources of sulfur are inadequate hydrotreating, hydrotreating stripper upsets and the recombination of hydrogen sulfide and olefins at high temperature and low pressures. The principal sources of nitrogen are inadequate hydrotreating, cracked naphtha in the feedstock, and improper use of inhibitors. Since the reforming unit catalyst can be quite sensitive to impurities, in certain embodiments sulfur and nitrogen levels are reduced in the hydrotreating process to provide a reformer feedstream meeting the requisite specification.

The separated light gases 130, 135, 140, 140, 150 are passed into one or more refinery gas analyzers 160, for instance in certain embodiments gas chromatographs that analyze the gases in accordance with ASTM D1945.

Liquid reformate 155 is fed into PIONA analyzer 165. In certain embodiments PIONA analyzer 165 is a gas chromatograph that analyzes the liquid in accordance with ASTM D6839. In the PIONA analysis, fractions of the reformate are tabulated by carbon number and n-paraffins, i-paraffins, naphthenes and aromatics, showing the percentage volume for each carbon number. In certain embodiments, the reformate is derived from straight-run naphtha from crude oil distillation, as opposed to being derived from intermediate refinery naphtha from cracking reactions, and accordingly no or few olefins are present.

Figure 2:
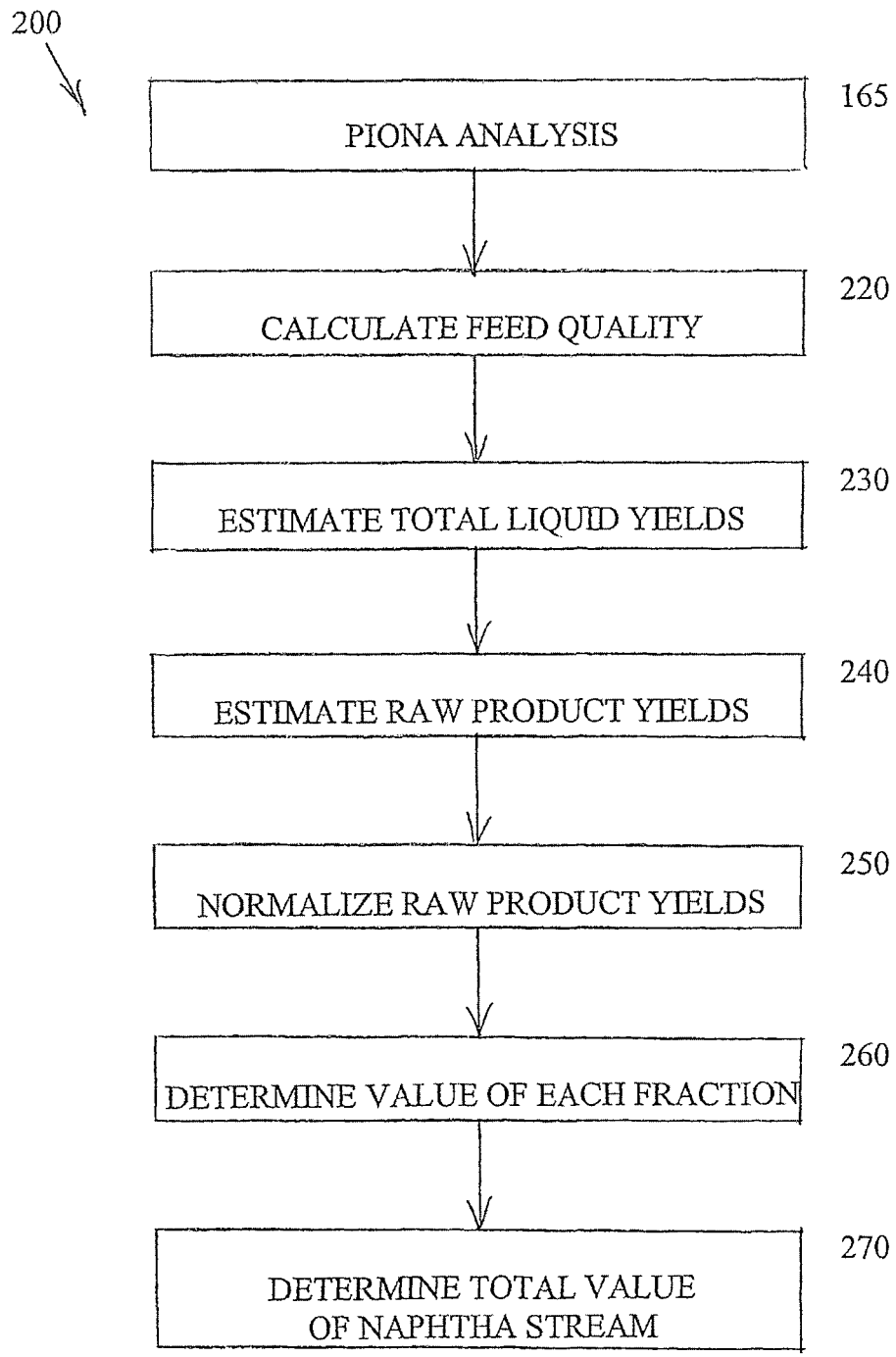
FIG. 2 is a process flow diagram of additional steps carried out to establish a value for naphtha streams using the system and method herein.

FIG. 2 shows a process flowchart of steps in a method according to one embodiment herein that occur after the analysis 210 of the crude oil sample or analysis of the reformate, to obtain data indicative of the naphthenes and aromatics present in the naphtha sample subject to valuation.

In certain embodiments, the analysis step 210 is a PIONA analysis of reformate 155. Variable N is used to represent the total percentage of naphthenes by volume, and variable A is used to represent the total percentage of aromatics by volume, as derived from the PIONA analysis.

In further embodiments, the analysis step 210 is an analysis of a crude oil sample selected from any one of Fourier transform near infrared spectroscopy, Fourier transform infrared spectroscopy, Fourier transform ion cyclotron mass spectroscopy, time of flight mass spectroscopy, near infrared spectroscopy, ultraviolet visible spectroscopy, laser induced ultraviolet spectroscopy, nuclear magnetic spectroscopy, fluorescence spectroscopy, Raman spectroscopy, gas chromatography, liquid chromatography, supercritical fluid chromatography, Thermogravimetric analysis, or differential scanning calorimetry. One of these analyses is used to assign an index to the crude oil sample. The assigned index is used to assign the aromatic content and the naphthene content of the naptha fraction subject to valuation.

In one embodiment, in which Fourier transform near infrared spectroscopy is used for the analysis step 210, an index (near infrared absorption index NIRA) is assigned according to equation (1):

$$NIRA = \sum_{i=4,000}^{12,821} (Absorbance_{(i)})/10,000 \tag{1a}$$

where:
Absorbance=absorbance value of the crude oil solution for peaks detected over a predetermined wavenumber range, e.g., over the range 4,000 cm$^{-1}$ to 12,821 cm$^{-1}$.

Using this index and the density of the crude oil sample, the aromatic and naphthene contents are calculated and assigned:

$$\text{Paraffin Content} = KPa + KPb*DEN + KPc*DEN^2 + KPd*DEN^3 + KPe*I + KPf*I^2 + KPg*I^3 + KPh*DEN*I \tag{1b}$$

$$\text{Aromatic Content} = KAa + KAb*DEN + KAc*DEN^2 + KAd*DEN^3 + KAe*I + KAf*I^2 + KAg*I^3 + KAh*DEN*I \tag{1c}$$

$$\text{Naphthene Content} = 100 - \text{Paraffin Content} - \text{Aromatic Content} \tag{1d}$$

where;
where KPa through KPh and KAa through KAh are constants,
DEN=Density of crude oil at 15° C., and
I=Index, e.g., FT NIR index as assigned in equation (1), or other index assigned from other analysis of the crude oil sample.

In step 220, the feed quality is calculated as:

$$\text{Feed quality} = N + 2A \tag{2}$$

Equations for determining the total reformer yield can be developed, in certain embodiments using linear regression of the N+2A concentration versus total yield.

In step 230, the total liquid yield, Y, is estimated as a function of the feed quality and the constant RON number (i.e., the target number), Rt:

$$Y = KYa*(N+2A)^2 + KYb*(N+2A) + KYc*Rt^2 + KYd*Rt + KYe \tag{3}$$

where KYa through KYe are constants.

The individual yields for H2, C1, C2, C3, C4 and C5+ and the reformate yield can then be assigned. In certain embodiments these assigned values are calculated using linear regression of the total reformate yield versus individual yields at the targeted octane number. In step 240, the estimated raw product yields for methane, ethane, propane, butane and gasoline are modeled linearly based upon the total liquid products variable, while hydrogen is modeled linearly based upon the total liquid products variable and the constant RON number, Rt.

$$\text{Raw Methane Yield, } C1r = KC1ra*Y + KC1rb \tag{4}$$

$$\text{Raw Ethane Yield, } C2r = KC2ra*Y + KC2rb \tag{5}$$

$$\text{Raw Propane Yield, } C3r = KC3ra*Y + KC3rb \tag{6}$$

$$\text{Raw Butane Yield, } C4r = KC4ra*Y + KC4rb \tag{7}$$

$$\text{Raw Gasoline Yield, } Gr = KGra*Y + KGrb \tag{8}$$

$$\text{Raw Hydrogen Yield, } Hr = KHra*Y + KHrb*Rt + KHrc \tag{9}$$

where KC1ra through KC4rb, KGra, KGrb, and KHRA through KHrc are constants.

The estimated total raw yield is the sum of the estimated raw yields for these components:

$$\text{Total Raw Yield, } Tr = C1r + C2r + C3r + C4r + Gr + Hr \tag{10}$$

In step 250, the yields are normalized to 100 by dividing the individual raw yields by the total raw yields, as follows:

$$\text{Normalized Methane Yield, } C1n = (C1r*100)/Tr \tag{11}$$

$$\text{Normalized Ethane Yield, } C2n = (C2r*100)/Tr \tag{12}$$

Normalized Propane Yield, $C3n=(C3r*100)/Tr$ (13)

Normalized Butane Yield, $C4n=(C4r*100)/Tr$ (14)

Normalized Gasoline Yield, $Gn=(Gr*100)/Tr$ (15)

Normalized Hydrogen Yield, $Hn=(Hr*100)/Tr$ (16)

In step 260, the estimated yield of each fraction is multiplied by its unit value, to assign a value to each fraction:

Value of Methane, $C1v=(C1n/100)*C1P$, where $C1P$ is methane's value (17)

Value of Ethane, $C2v=(C2n/100)*C2P$, where $C2P$ is ethane's value (18)

Value of Propane, $C3v=(C3n/100)*C3P$, where $C3P$ is propane's value (19)

Value of Butane, $C4v=(C4n/100)*C4P$, where $C4P$ is butane's value (20)

Value of Gasoline, $Gv=(Gn/100)*GP$, where $GP$ is gasoline's value (21)

Value of Hydrogen, $Hv=(Hn/100)*HP$, where $HP$ is hydrogen's value (22)

In step 270, the total value of the naphtha stream is then estimated by summing the calculated values of the individual streams:

Naphtha Unit Value($/ton), $NPT=C1v+C2v+C3v+C4v+Gv+Hv$ (23)

The value of the naphtha stream can also be restated as $/barrel, by dividing the value expressed as $/ton by the density and multiplying by the number of liters in a barrel of oil (159 liters/barrel):

$NPB=(NPT/Density)*159$ liters/barrel (24)

When two naphtha streams are to be evaluated, this process can readily be used to assign values to each for comparison.

Figure 3:
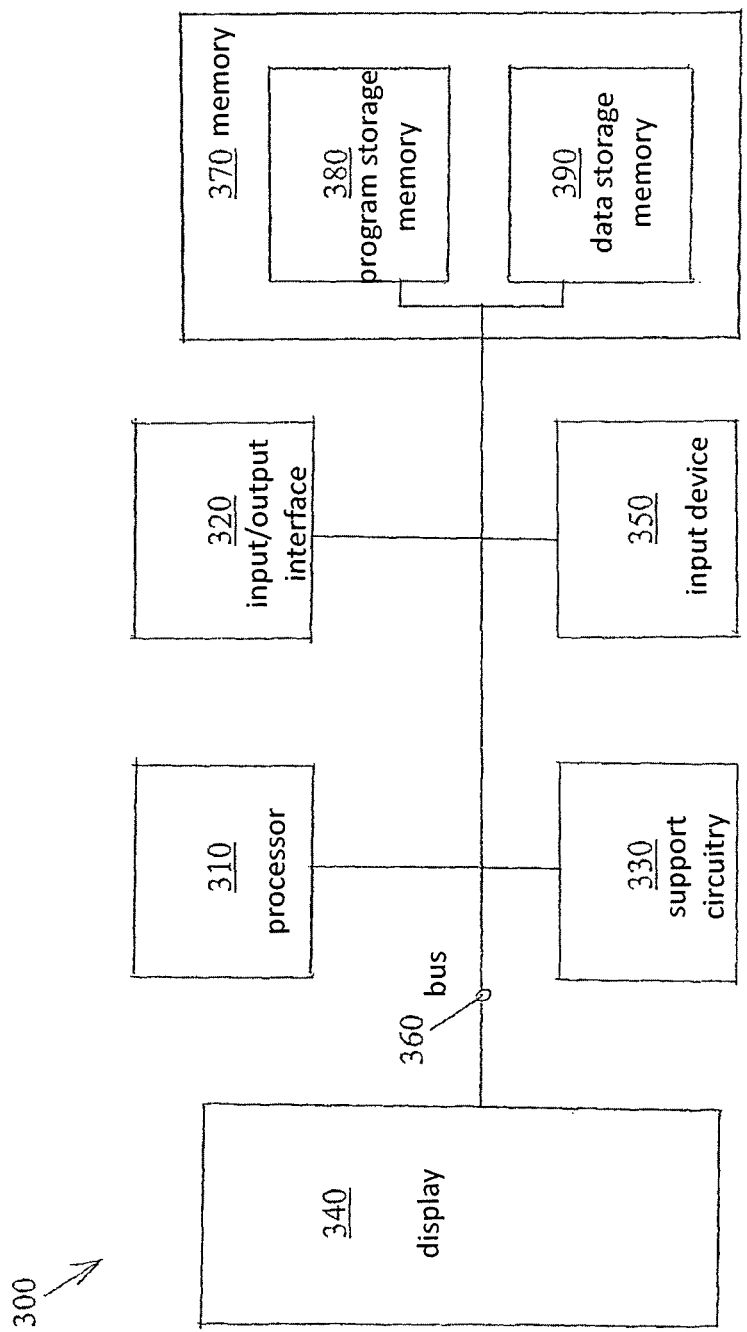
FIG. 3 is a block diagram of a component of a system for implementing the invention according to one embodiment.

An exemplary block diagram of a computer system 300 by which calculation modules are operable, for instance, to carry out all or a portion of equations (1a)-(24), can be implemented is shown in FIG. 3. Computer system 300 includes a processor 310, such as a central processing unit, an input/output interface 320 and support circuitry 330. In certain embodiments, where the computer 300 requires direct human interaction, a display 340 and an input device 350 such as a keyboard, mouse or pointer are also provided. The display 340, input device 350, processor 310, input/output interface 320 and support circuitry 330 are shown connected to a bus 360 which also connects to a memory unit 370. Memory 370 includes program storage memory 380 and data storage memory 390. Note that while computer 300 is depicted with the direct human interface components of display 340 and input device 350, programming of modules and importation and exportation of data can also be accomplished over the interface 320, for instance, where the computer 300 is connected to a network and the programming and display operations occur on another associated computer, or via a detachable input device, as are well known in the art for interfacing programmable logic controllers.

Program storage memory 380 and data storage memory 390 can each comprise volatile (RAM) and non-volatile (ROM) memory units and can also comprise hard disk and backup storage capacity, and both program storage memory 380 and data storage memory 390 can be embodied in a single memory device or separated in plural memory devices. Program storage memory 380 stores software program modules and associated data, including one or more calculation modules such as a feed quality calculation module (e.g., corresponding to step 220 described above with respect to FIG. 2), yield calculation modules (e.g., corresponding to steps 230, 240 and 250 described above with respect to FIG. 2, including separate or individual modules for total reformer yield; total liquid yield; individual yields for H2, C1, C2, C3, C4 and C5+ and the reformate; total raw yield; and normalized yields), and valuation modules (e.g., corresponding to steps 260 and 270 described above with respect to FIG. 2). Data storage memory 390 stores data used and/or generated by the one or more modules of the present system, including PIONA analysis data or portions thereof used by the one or more modules of the present system, and calculated feed quality, yields and valuations generated by the one or more modules of the present system.

The calculated and assigned results in accordance with the systems and methods herein are displayed, audibly outputted, printed, and/or stored to memory for use as described herein.

It is to be appreciated that the computer system 300 can be any general or special purpose computer such as a personal computer, minicomputer, workstation, mainframe, a dedicated controller such as a programmable logic controller, or a combination thereof. While the computer system 300 is shown, for illustration purposes, as a single computer unit, the system can comprise a group/farm of computers which can be scaled depending on the processing load and database size, e.g., the total number of samples that are processed and results maintained on the system. The computer system 300 can serve as a common multi-tasking computer.

The computing device 300 preferably supports an operating system, for example, stored in program storage memory 390 and executed by the processor 310 from volatile memory. According to the present system and method, the operating system contains instructions for interfacing the device 300 to the calculation module(s). According to an embodiment of the invention, the operating system contains instructions for interfacing computer system 300 to the Internet and/or to private networks.

EXAMPLE 1

An exemplary PIONA analysis of a sample from a hydrotreated naphtha stream is shown in Table 1. Note that while most of the light components such as propane and butane present in the naphtha are separated, some light components will remain dissolved in the liquid reformate product, and thus will appear in the PIONA analysis.

TABLE 1

PIONA ANALYSIS OF A NAPHTHA STREAM
Hydrocarbon Family

| Carbon # | n-Paraffins | i-Paraffins | Naphthenes | Aromatics |
|---|---|---|---|---|
| C3 | 0.112% | 0% | 0% | 0% |
| C4 | 2.022% | 0.212% | 0% | 0% |
| C5 | 6.232% | 2.626% | 0.494% | 0% |
| C6 | 8.697% | 6.114% | 3.086% | 0.751% |
| C7 | 12.749% | 16.033% | 5.545% | 1.985% |
| C8 | 5.288% | 6.006% | 3.017% | 2.448% |
| C9 | 3.02% | 3.829% | 2.019% | 1.893% |

TABLE 1-continued

PIONA ANALYSIS OF A NAPHTHA STREAM
Hydrocarbon Family

| Carbon # | n-Paraffins | i-Paraffins | Naphthenes | Aromatics |
|---|---|---|---|---|
| C10 | 1.304% | 2.159% | 0.819% | 0.968% |
| C11 | 0.084% | 0.25% | 0.221% | 0.017% |
| Total* | 37.29% | 36.77% | 14.98% | 8.05% |

*Total = 97.09 V %, losses = 2.91 V %. (i.e., the yields are not normalized.)

Based on the data of Table 1, equations (2)-(24) can be used to assign the naptha value as a function of the feed quality and the target RON number, Rt. Thus, in the example given in Table 1, N=14.98, and A=8.05

$$\text{Feed quality}=N+2A=14.98+2*8.05=31.08 \quad (2).$$

Equations and constants for assigning total reformer yield were developed from a linear regression of the N+2A concentration versus total yield. The individual yields for H2, C1, C2, C3, C4 and C5+ and the reformate yield were calculated from a linear regression of the total reformate yield versus individual yields at the target research octane number. For these calculations, the following constants are applied:

$$KYa=0.01702; KYb=2.192; KYc=-0.03333;$$
$$KYd=5.531; \text{ and } KYe=-206.63 \quad \text{Eq. (3):}$$

$$KC1ra=-0.12393; KC1rb=11.42; KC2ra=-0.17991;$$
$$KC2rb=16.8; KC3ra=-0.25714;$$
$$KC3rb=24.24286; KC4ra=-0.28705;$$
$$KC4rb=27.27143; KGra=0.839255;$$
$$KGrb=18.09532; KHra=0.0605; KHrb=0.1;$$
$$\text{and } KHrc=-12.145. \quad \text{Eqs.(4)-(9):}$$

Thus, for the example given in Table 1, when a target octane number for gasoline of 98 is selected, the yield equation (3) is as follows:

$$Y=KYa*(N+2A)^2+KYb*(N+2A)+KYc*Rt^2+KYd*Rt+KYe \quad (3)$$

$$Y=(-0.01702)*(31.08)^2+2.192*31.08-0.03333*(98)^2+5.531*98-206.63$$

$$Y=66.99.$$

The individual raw product yields are as follows:

$$C1r=KC1ra*Y+KC1rb=0.12393*66.99+11.42=3.11 \quad (4)$$

$$C2r=KC2ra*Y+KC2rb=-0.17991*66.99+16.8=4.75 \quad (5)$$

$$C3r=KC3ra*Y+KC3rb=-0.25714*66.99+24.24286=7.02 \quad (6)$$

$$C4r=KC4ra*Y+KC4rb=-0.28705*66.99+27.27143=8.04 \quad (7)$$

$$Gr=KGra*Y+KGrb=0.839255*66.99+18.09532=74.32 \quad (8)$$

$$Hr=KHra*Y+KHrb*Rt+KHrc=0.0605*66.99+0.1*98-12.145=1.7 \quad (9)$$

The Total Raw Yield is:

$$Tr = C1r + C2r + C3r + C4r + Gr + Hr \quad (10)$$
$$= 3.11 + 4.75 + 7.02 + 8.04 + 74.32 + 1.71$$
$$= 98.95$$

The normalized product yields are as follows:

$$C1n=(C1r*100)/Tr=(3.11*100)/98.94917=3.14 \quad (11)$$

$$C2n=(C2r*100)/Tr=(4.75*100)/98.94917=4.80 \quad (12)$$

$$C3n=(C3r*100)/Tr=(7.02*100)/98.94917=7.09 \quad (13)$$

$$C4n=(C4r*100)/Tr=(8.04*100)/98.94917=8.13 \quad (14)$$

$$Gn=(Gr*100)/Tr=(74.32*100)/98.94917=75.11 \quad (15)$$

$$Hn=(Hr*100)/Tr(1.71*100)/98.94917=1.73 \quad (16)$$

Thus, if unit values are, for methane, C1P=$152.44/ton; for ethane, C2P=$149.81/ton; for propane, C3P=$343.71/ton; for butane, C4P=$499.03/ton; for gasoline, GP=$601.63/ton; and for hydrogen, HP=$391.60/ton, then the value of those products in the naphtha stream of Table 1 would be calculated as:

$$C1v=(3.14/100)*\$152.44/\text{ton}=\$4.80/\text{ton} \quad (17)$$

$$C2v=(4.80/100)*\$149.81/\text{ton}=\$7.19/\text{ton} \quad (18)$$

$$C3v=(7.09/100)*\$343.71/\text{ton}=\$24.37/\text{ton} \quad (19)$$

$$C4v=(8.13/100)*\$499.03/\text{ton}=\$40.57/\text{ton} \quad (20)$$

$$Gv=(75.11/100)*\$601.63/\text{ton}=\$451.88/\text{to} \quad (21)$$

$$Hv=(1.73/100)*\$391.60/\text{ton}=\$6.77/\text{ton} \quad (22)$$

The value of the naphtha stream calculated by this method is:

$$NPT=4.80+7.19+24.37+40.57+451.88+6.77=\$535.58/\text{ton} \quad (23)$$

$$NPB=(\$535.58/\text{ton}/750 \text{ liters/ton})*159 \text{ liters/barrel}=\$113.54/\text{barrel} \quad (24)$$

EXAMPLE 2

A sample of Arabian light crude with a density of 0.8658 Kg/l at 15° C. was analyzed by near infrared spectroscopy. The spectra data is presented in Table 3. The near infrared spectroscopy index (NIRA) is calculated using equation (1a), by summing the absorbances (columns C2=1674.09, C4=1667.16, C6=1847.95, C8=1075.85, C10=1136.82) of the detected peaks (Table 3) and then dividing by 10,000, with the value in the example calculated as 0.7402.

NIRA, which is calculated using the equation 1b by taking the sums of absorbance (columns C2=1685.305, C4=1678.383, C6=1949.850, C8=1120.099, C10=1142.337) in Table 3, is 0.7575974. The paraffin, aromatic and naphthenic contents of the naphtha fraction boiling in the range 36° C.-180° C. are calculated using the equations 1b, 1c and 1d:

$$\text{Paraffin Content}=KPa+KPb*DEN+KPc*DEN^2+KPd*DEN^3+KPe*I+KPf*I^2+KPg*I^3+KPh*DEN*I \quad (1b)$$

$$\text{Aromatic Content}=KAa+KAb*DEN+KAc*DEN^2+KAd*DEN^3+KAe*I+KAf*I^2+KAg*I^3+KAh*DEN*I \quad (1c)$$

$$\text{Naphthene Content}=100-\text{Paraffin Content}-\text{Aromatic Content} \quad (1d)$$

Constants KPa through KPh and KAa through KAh were determined using linear regression and shown in Table 2, with the calculated values presented in the tables according to Equations (1b) and (1c).

TABLE 2

| Constants | Values | Variable | Values | Equation | Value |
|---|---|---|---|---|---|
| KPa | 1.7341106E+06 | — | | Kpa | 1.734E+06 |
| Kpb | −5.7388549E+06 | DEN | 8.658E−01 | Kpb * DEN | −4.969E+06 |
| KPc | 6.2814681E+06 | DEN^2 | 7.496E−01 | Kpc * DEN^2 | 4.709E+06 |
| KPd | −2.2726340E+06 | DEN^3 | 6.490E−01 | Kpd * DEN^3 | −1.475E+06 |
| Kpe | 4.3445704E+04 | I | 7.402E−01 | Kpe * NIRA | 3.216E+04 |
| KPf | −7.6959428E+03 | I^2 | 5.479E−01 | Kpf * NIRA^2 | −4.217E+03 |
| KPg | 4.2917337E+03 | I^3 | 4.056E−01 | Kpg * NIRA^3 | 1.741E+03 |
| KPh | −4.4780051E+04 | DEN * I | 6.409E−01 | Kph * DEN * NIRA | −2.870E+04 |
| Paraffins | | | | Paraffins | 76.86 |
| KPa | 3.5428498E+05 | — | | KPa | 3.543E+05 |
| Kpb | −1.2231660E+06 | DEN | 8.658E−01 | Kpb * DEN | −1.059E+06 |
| KPc | 1.4074133E+06 | DEN^2 | 7.496E−01 | KPc * DEN^2 | 1.055E+06 |
| KPd | −5.3968374E+05 | DEN^3 | 6.490E−01 | KPd * DEN^3 | −3.503E+05 |
| Kpe | −1.8696110E+02 | I | 7.402E−01 | Kpe * I | −1.384E+02 |
| KPf | 1.0846669E+02 | I^2 | 5.479E−01 | KPf * I^2 | 5.943E+01 |
| KPg | −7.3293203E+01 | I^3 | 4.056E−01 | KPg * I^3 | −2.972E+01 |
| KPh | 1.5524161E+02 | DEN * I | 6.409E−01 | KPh * DEN * I | 9.949E+01 |
| Aromatics | | | | Aromatics | 8.05 |

The actual and predicted values are compared as follows and the correlation predicts the paraffin and aromatic composition of the naphtha fraction very accurately. The paraffins contents are: Actual 76.74 V % vs. predicted 76.68 V %. The aromatics contents are: Actual 8.05 V % vs. predicted 8.05 V %. These values are used in equations 2-24 to calculate the naphtha value.

In alternate embodiments, the present invention can be implemented as a computer program product for use with a computerized computing system. Those skilled in the art will readily appreciate that programs defining the functions of the present invention can be written in any appropriate programming language and delivered to a computer in any form, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the system embodiments can incorporate a variety of computer readable media that comprise a computer usable medium having computer readable code means embodied therein. One skilled in the art will recognize that the software associated with the various processes described can be embodied in a wide variety of computer accessible media from which the software is loaded and activated. Pursuant to In re Beauregard, 35 USPQ2d 1383 (U.S. Pat. No. 5,710,578), the present invention contemplates and includes this type of computer readable media within the scope of the invention. In certain embodiments, pursuant to In re Nuijten, 500 F.3d 1346 (Fed. Cir. 2007) (U.S. patent application Ser. No. 09/211,928), the scope of the present claims is limited to computer readable media, wherein the media is both tangible and non-transitory.

The system and method of the present invention have been described above and with reference to the attached drawings; however, modifications will be apparent to those of ordinary skill in the art and the scope of protection for the invention is to be defined by the claims that follow.

TABLE 3

| C1 WL, nm | C2 Abs., % | C3 WL, nm | C4 Abs., % | C5 WL, nm | C6 Abs., % | C7 WL, nm | C8 Abs., % | C9 WL, nm | C10 Abs., % |
|---|---|---|---|---|---|---|---|---|---|
| 12493 | 3.51 | 10792 | 3.59 | 9091 | 4.28 | 7390 | 2.98 | 5689 | 3.15 |
| 12489 | 3.47 | 10788 | 3.59 | 9087 | 4.32 | 7386 | 2.98 | 5685 | 3.18 |
| 12485 | 3.47 | 10784 | 3.59 | 9084 | 4.34 | 7383 | 2.98 | 5682 | 3.20 |
| 12482 | 3.47 | 10781 | 3.59 | 9080 | 4.33 | 7379 | 2.98 | 5678 | 3.21 |
| 12478 | 3.44 | 10777 | 3.59 | 9076 | 4.33 | 7375 | 2.99 | 5674 | 3.22 |
| 12474 | 3.43 | 10773 | 3.57 | 9072 | 4.33 | 7371 | 2.99 | 5670 | 3.20 |
| 12470 | 3.45 | 10769 | 3.56 | 9068 | 4.29 | 7367 | 2.99 | 5666 | 3.17 |
| 12466 | 3.45 | 10765 | 3.56 | 9064 | 4.25 | 7363 | 2.99 | 5662 | 3.12 |
| 12462 | 3.42 | 10761 | 3.56 | 9060 | 4.26 | 7359 | 2.99 | 5658 | 3.06 |
| 12458 | 3.41 | 10757 | 3.56 | 9057 | 4.35 | 7356 | 3.00 | 5655 | 3.00 |
| 12455 | 3.49 | 10754 | 3.57 | 9053 | 4.45 | 7352 | 3.00 | 5651 | 2.94 |
| 12451 | 3.56 | 10750 | 3.58 | 9049 | 4.44 | 7348 | 3.00 | 5647 | 2.88 |
| 12447 | 3.53 | 10746 | 3.57 | 9045 | 4.33 | 7344 | 3.00 | 5643 | 2.82 |
| 12443 | 3.43 | 10742 | 3.54 | 9041 | 4.27 | 7340 | 2.99 | 5639 | 2.76 |
| 12439 | 3.39 | 10738 | 3.54 | 9037 | 4.29 | 7336 | 2.99 | 5635 | 2.70 |
| 12435 | 3.46 | 10734 | 3.57 | 9033 | 4.39 | 7332 | 2.99 | 5631 | 2.64 |
| 12431 | 3.52 | 10730 | 3.62 | 9030 | 4.46 | 7329 | 2.98 | 5628 | 2.58 |
| 12428 | 3.52 | 10727 | 3.64 | 9026 | 4.44 | 7325 | 2.98 | 5624 | 2.52 |
| 12424 | 3.55 | 10723 | 3.62 | 9022 | 4.38 | 7321 | 2.97 | 5620 | 2.46 |
| 12420 | 3.58 | 10719 | 3.59 | 9018 | 4.36 | 7317 | 2.97 | 5616 | 2.41 |
| 12416 | 3.55 | 10715 | 3.57 | 9014 | 4.38 | 7313 | 2.97 | 5612 | 2.36 |
| 12412 | 3.52 | 10711 | 3.60 | 9010 | 4.40 | 7309 | 2.97 | 5608 | 2.32 |

TABLE 3-continued

| C1 WL, nm | C2 Abs., % | C3 WL, nm | C4 Abs., % | C5 WL, nm | C6 Abs., % | C7 WL, nm | C8 Abs., % | C9 WL, nm | C10 Abs., % |
|---|---|---|---|---|---|---|---|---|---|
| 12408 | 3.51 | 10707 | 3.60 | 9006 | 4.42 | 7305 | 2.97 | 5604 | 2.28 |
| 12404 | 3.56 | 10703 | 3.57 | 9003 | 4.44 | 7302 | 2.97 | 5601 | 2.25 |
| 12401 | 3.61 | 10700 | 3.55 | 8999 | 4.42 | 7298 | 2.97 | 5597 | 2.23 |
| 12397 | 3.58 | 10696 | 3.55 | 8995 | 4.43 | 7294 | 2.97 | 5593 | 2.21 |
| 12393 | 3.52 | 10692 | 3.57 | 8991 | 4.46 | 7290 | 2.97 | 5589 | 2.20 |
| 12389 | 3.51 | 10688 | 3.60 | 8987 | 4.47 | 7286 | 2.97 | 5585 | 2.18 |
| 12385 | 3.51 | 10684 | 3.62 | 8983 | 4.47 | 7282 | 2.98 | 5581 | 2.18 |
| 12381 | 3.47 | 10680 | 3.65 | 8979 | 4.51 | 7278 | 2.98 | 5577 | 2.17 |
| 12377 | 3.43 | 10676 | 3.68 | 8976 | 4.55 | 7275 | 2.98 | 5574 | 2.16 |
| 12374 | 3.39 | 10673 | 3.67 | 8972 | 4.57 | 7271 | 2.98 | 5570 | 2.16 |
| 12370 | 3.38 | 10669 | 3.64 | 8968 | 4.52 | 7267 | 2.98 | 5566 | 2.15 |
| 12366 | 3.41 | 10665 | 3.61 | 8964 | 4.49 | 7263 | 2.99 | 5562 | 2.15 |
| 12362 | 3.47 | 10661 | 3.61 | 8960 | 4.54 | 7259 | 2.99 | 5558 | 2.14 |
| 12358 | 3.54 | 10657 | 3.63 | 8956 | 4.69 | 7255 | 2.99 | 5554 | 2.14 |
| 12354 | 3.56 | 10653 | 3.66 | 8952 | 4.82 | 7251 | 3.00 | 5550 | 2.13 |
| 12350 | 3.54 | 10649 | 3.67 | 8949 | 4.79 | 7248 | 3.00 | 5547 | 2.12 |
| 12347 | 3.53 | 10646 | 3.67 | 8945 | 4.69 | 7244 | 3.00 | 5543 | 2.11 |
| 12343 | 3.55 | 10642 | 3.65 | 8941 | 4.64 | 7240 | 3.00 | 5539 | 2.11 |
| 12339 | 3.57 | 10638 | 3.61 | 8937 | 4.58 | 7236 | 3.00 | 5535 | 2.10 |
| 12335 | 3.52 | 10634 | 3.57 | 8933 | 4.55 | 7232 | 3.00 | 5531 | 2.10 |
| 12331 | 3.43 | 10630 | 3.58 | 8929 | 4.62 | 7228 | 3.00 | 5527 | 2.09 |
| 12327 | 3.41 | 10626 | 3.61 | 8925 | 4.72 | 7224 | 3.00 | 5523 | 2.09 |
| 12323 | 3.48 | 10622 | 3.62 | 8922 | 4.78 | 7221 | 3.00 | 5520 | 2.09 |
| 12320 | 3.60 | 10619 | 3.62 | 8918 | 4.79 | 7217 | 3.00 | 5516 | 2.09 |
| 12316 | 3.64 | 10615 | 3.61 | 8914 | 4.77 | 7213 | 3.01 | 5512 | 2.09 |
| 12312 | 3.65 | 10611 | 3.60 | 8910 | 4.68 | 7209 | 3.01 | 5508 | 2.09 |
| 12308 | 3.66 | 10607 | 3.60 | 8906 | 4.79 | 7205 | 3.02 | 5504 | 2.09 |
| 12304 | 3.64 | 10603 | 3.61 | 8902 | 5.04 | 7201 | 3.02 | 5500 | 2.09 |
| 12300 | 3.59 | 10599 | 3.63 | 8898 | 4.97 | 7197 | 3.02 | 5496 | 2.09 |
| 12296 | 3.58 | 10595 | 3.66 | 8895 | 4.89 | 7194 | 3.03 | 5493 | 2.09 |
| 12293 | 3.64 | 10592 | 3.65 | 8891 | 4.94 | 7190 | 3.03 | 5489 | 2.08 |
| 12289 | 3.70 | 10588 | 3.62 | 8887 | 4.93 | 7186 | 3.03 | 5485 | 2.08 |
| 12285 | 3.72 | 10584 | 3.63 | 8883 | 4.86 | 7182 | 3.02 | 5481 | 2.07 |
| 12281 | 3.67 | 10580 | 3.64 | 8879 | 4.83 | 7178 | 3.02 | 5477 | 2.07 |
| 12277 | 3.60 | 10576 | 3.62 | 8875 | 4.82 | 7174 | 3.01 | 5473 | 2.06 |
| 12273 | 3.56 | 10572 | 3.61 | 8871 | 4.76 | 7170 | 3.00 | 5469 | 2.05 |
| 12269 | 3.52 | 10568 | 3.62 | 8868 | 4.83 | 7167 | 2.98 | 5466 | 2.04 |
| 12266 | 3.49 | 10565 | 3.61 | 8864 | 4.91 | 7163 | 2.97 | 5462 | 2.03 |
| 12262 | 3.50 | 10561 | 3.62 | 8860 | 4.93 | 7159 | 2.95 | 5458 | 2.02 |
| 12258 | 3.53 | 10557 | 3.64 | 8856 | 4.88 | 7155 | 2.93 | 5454 | 2.01 |
| 12254 | 3.53 | 10553 | 3.64 | 8852 | 4.84 | 7151 | 2.92 | 5450 | 2.00 |
| 12250 | 3.50 | 10549 | 3.63 | 8848 | 4.78 | 7147 | 2.91 | 5446 | 1.98 |
| 12246 | 3.50 | 10545 | 3.63 | 8844 | 4.67 | 7143 | 2.90 | 5442 | 1.97 |
| 12242 | 3.51 | 10541 | 3.63 | 8841 | 4.66 | 7140 | 2.89 | 5439 | 1.96 |
| 12239 | 3.53 | 10538 | 3.66 | 8837 | 4.79 | 7136 | 2.88 | 5435 | 1.94 |
| 12235 | 3.56 | 10534 | 3.69 | 8833 | 4.89 | 7132 | 2.87 | 5431 | 1.93 |
| 12231 | 3.57 | 10530 | 3.68 | 8829 | 4.89 | 7128 | 2.87 | 5427 | 1.91 |
| 12227 | 3.57 | 10526 | 3.65 | 8825 | 4.95 | 7124 | 2.86 | 5423 | 1.90 |
| 12223 | 3.57 | 10522 | 3.63 | 8821 | 5.05 | 7120 | 2.86 | 5419 | 1.88 |
| 12219 | 3.57 | 10518 | 3.63 | 8817 | 4.95 | 7116 | 2.86 | 5415 | 1.87 |
| 12215 | 3.55 | 10514 | 3.65 | 8814 | 4.73 | 7113 | 2.85 | 5412 | 1.85 |
| 12212 | 3.56 | 10511 | 3.66 | 8810 | 4.66 | 7109 | 2.85 | 5408 | 1.83 |
| 12208 | 3.65 | 10507 | 3.65 | 8806 | 4.67 | 7105 | 2.85 | 5404 | 1.82 |
| 12204 | 3.70 | 10503 | 3.63 | 8802 | 4.71 | 7101 | 2.86 | 5400 | 1.80 |
| 12200 | 3.64 | 10499 | 3.63 | 8798 | 4.82 | 7097 | 2.86 | 5396 | 1.79 |
| 12196 | 3.56 | 10495 | 3.65 | 8794 | 5.12 | 7093 | 2.86 | 5392 | 1.77 |
| 12192 | 3.51 | 10491 | 3.66 | 8790 | 5.40 | 7089 | 2.86 | 5388 | 1.76 |
| 12188 | 3.50 | 10487 | 3.64 | 8787 | 5.07 | 7086 | 2.86 | 5385 | 1.74 |
| 12185 | 3.51 | 10484 | 3.61 | 8783 | 4.95 | 7082 | 2.86 | 5381 | 1.73 |
| 12181 | 3.53 | 10480 | 3.58 | 8779 | 4.88 | 7078 | 2.85 | 5377 | 1.72 |
| 12177 | 3.55 | 10476 | 3.58 | 8775 | 4.78 | 7074 | 2.85 | 5373 | 1.71 |
| 12173 | 3.59 | 10472 | 3.61 | 8771 | 4.88 | 7070 | 2.84 | 5369 | 1.70 |
| 12169 | 3.59 | 10468 | 3.66 | 8767 | 4.99 | 7066 | 2.83 | 5365 | 1.69 |
| 12165 | 3.52 | 10464 | 3.68 | 8763 | 5.15 | 7062 | 2.82 | 5361 | 1.68 |
| 12161 | 3.47 | 10460 | 3.69 | 8760 | 4.98 | 7059 | 2.80 | 5358 | 1.67 |
| 12158 | 3.49 | 10457 | 3.70 | 8756 | 4.85 | 7055 | 2.79 | 5354 | 1.67 |
| 12154 | 3.57 | 10453 | 3.74 | 8752 | 4.77 | 7051 | 2.78 | 5350 | 1.66 |
| 12150 | 3.61 | 10449 | 3.77 | 8748 | 4.82 | 7047 | 2.77 | 5346 | 1.66 |
| 12146 | 3.61 | 10445 | 3.78 | 8744 | 4.95 | 7043 | 2.76 | 5342 | 1.66 |
| 12142 | 3.61 | 10441 | 3.77 | 8740 | 5.06 | 7039 | 2.75 | 5338 | 1.65 |
| 12138 | 3.58 | 10437 | 3.73 | 8736 | 5.05 | 7035 | 2.74 | 5334 | 1.65 |
| 12134 | 3.54 | 10433 | 3.70 | 8733 | 4.89 | 7032 | 2.73 | 5331 | 1.65 |
| 12131 | 3.53 | 10430 | 3.69 | 8729 | 4.83 | 7028 | 2.72 | 5327 | 1.65 |
| 12127 | 3.52 | 10426 | 3.69 | 8725 | 4.85 | 7024 | 2.72 | 5323 | 1.65 |
| 12123 | 3.51 | 10422 | 3.69 | 8721 | 4.92 | 7020 | 2.71 | 5319 | 1.64 |
| 12119 | 3.53 | 10418 | 3.71 | 8717 | 5.02 | 7016 | 2.70 | 5315 | 1.64 |
| 12115 | 3.57 | 10414 | 3.76 | 8713 | 5.11 | 7012 | 2.70 | 5311 | 1.64 |

TABLE 3-continued

| C1 WL, nm | C2 Abs., % | C3 WL, nm | C4 Abs., % | C5 WL, nm | C6 Abs., % | C7 WL, nm | C8 Abs., % | C9 WL, nm | C10 Abs., % |
|---|---|---|---|---|---|---|---|---|---|
| 12111 | 3.60 | 10410 | 3.78 | 8709 | 5.00 | 7008 | 2.69 | 5307 | 1.63 |
| 12107 | 3.64 | 10406 | 3.76 | 8706 | 4.95 | 7005 | 2.69 | 5304 | 1.63 |
| 12104 | 3.64 | 10403 | 3.75 | 8702 | 4.96 | 7001 | 2.69 | 5300 | 1.63 |
| 12100 | 3.57 | 10399 | 3.77 | 8698 | 5.11 | 6997 | 2.68 | 5296 | 1.62 |
| 12096 | 3.51 | 10395 | 3.80 | 8694 | 5.20 | 6993 | 2.68 | 5292 | 1.62 |
| 12092 | 3.53 | 10391 | 3.80 | 8690 | 5.09 | 6989 | 2.68 | 5288 | 1.62 |
| 12088 | 3.56 | 10387 | 3.79 | 8686 | 4.97 | 6985 | 2.67 | 5284 | 1.62 |
| 12084 | 3.54 | 10383 | 3.79 | 8682 | 5.01 | 6981 | 2.67 | 5280 | 1.61 |
| 12080 | 3.51 | 10379 | 3.75 | 8679 | 5.07 | 6978 | 2.66 | 5277 | 1.61 |
| 12077 | 3.52 | 10376 | 3.71 | 8675 | 5.03 | 6974 | 2.66 | 5273 | 1.61 |
| 12073 | 3.57 | 10372 | 3.72 | 8671 | 5.03 | 6970 | 2.65 | 5269 | 1.60 |
| 12069 | 3.60 | 10368 | 3.76 | 8667 | 5.08 | 6966 | 2.64 | 5265 | 1.60 |
| 12065 | 3.57 | 10364 | 3.78 | 8663 | 4.95 | 6962 | 2.63 | 5261 | 1.60 |
| 12061 | 3.51 | 10360 | 3.78 | 8659 | 4.80 | 6958 | 2.63 | 5257 | 1.59 |
| 12057 | 3.50 | 10356 | 3.77 | 8655 | 4.75 | 6954 | 2.62 | 5253 | 1.59 |
| 12053 | 3.51 | 10352 | 3.77 | 8652 | 4.80 | 6951 | 2.61 | 5250 | 1.59 |
| 12050 | 3.51 | 10349 | 3.76 | 8648 | 4.95 | 6947 | 2.60 | 5246 | 1.58 |
| 12046 | 3.53 | 10345 | 3.77 | 8644 | 5.10 | 6943 | 2.60 | 5242 | 1.58 |
| 12042 | 3.55 | 10341 | 3.76 | 8640 | 4.92 | 6939 | 2.59 | 5238 | 1.58 |
| 12038 | 3.54 | 10337 | 3.73 | 8636 | 4.77 | 6935 | 2.58 | 5234 | 1.58 |
| 12034 | 3.53 | 10333 | 3.72 | 8632 | 4.71 | 6931 | 2.57 | 5230 | 1.57 |
| 12030 | 3.55 | 10329 | 3.76 | 8628 | 4.70 | 6927 | 2.57 | 5226 | 1.57 |
| 12026 | 3.60 | 10325 | 3.78 | 8625 | 4.77 | 6924 | 2.56 | 5223 | 1.57 |
| 12023 | 3.70 | 10322 | 3.75 | 8621 | 4.81 | 6920 | 2.55 | 5219 | 1.57 |
| 12019 | 3.78 | 10318 | 3.73 | 8617 | 4.77 | 6916 | 2.55 | 5215 | 1.57 |
| 12015 | 3.80 | 10314 | 3.76 | 8613 | 4.79 | 6912 | 2.54 | 5211 | 1.56 |
| 12011 | 3.92 | 10310 | 3.78 | 8609 | 4.81 | 6908 | 2.53 | 5207 | 1.56 |
| 12007 | 3.81 | 10306 | 3.77 | 8605 | 4.74 | 6904 | 2.53 | 5203 | 1.56 |
| 12003 | 3.77 | 10302 | 3.74 | 8601 | 4.75 | 6900 | 2.52 | 5199 | 1.55 |
| 11999 | 3.74 | 10298 | 3.72 | 8598 | 4.86 | 6897 | 2.51 | 5196 | 1.55 |
| 11996 | 3.72 | 10295 | 3.73 | 8594 | 5.08 | 6893 | 2.50 | 5192 | 1.55 |
| 11992 | 3.79 | 10291 | 3.76 | 8590 | 5.19 | 6889 | 2.49 | 5188 | 1.54 |
| 11988 | 3.85 | 10287 | 3.76 | 8586 | 5.06 | 6885 | 2.49 | 5184 | 1.54 |
| 11984 | 3.84 | 10283 | 3.75 | 8582 | 4.91 | 6881 | 2.48 | 5180 | 1.54 |
| 11980 | 3.84 | 10279 | 3.74 | 8578 | 4.79 | 6877 | 2.47 | 5176 | 1.53 |
| 11976 | 3.86 | 10275 | 3.72 | 8574 | 4.81 | 6873 | 2.46 | 5172 | 1.53 |
| 11972 | 3.79 | 10271 | 3.71 | 8571 | 4.92 | 6870 | 2.46 | 5169 | 1.53 |
| 11969 | 3.74 | 10268 | 3.69 | 8567 | 4.95 | 6866 | 2.45 | 5165 | 1.53 |
| 11965 | 3.80 | 10264 | 3.69 | 8563 | 4.99 | 6862 | 2.44 | 5161 | 1.52 |
| 11961 | 3.82 | 10260 | 3.73 | 8559 | 4.95 | 6858 | 2.44 | 5157 | 1.52 |
| 11957 | 3.80 | 10256 | 3.77 | 8555 | 4.80 | 6854 | 2.43 | 5153 | 1.52 |
| 11953 | 3.76 | 10252 | 3.76 | 8551 | 4.66 | 6850 | 2.43 | 5149 | 1.51 |
| 11949 | 3.74 | 10248 | 3.72 | 8547 | 4.62 | 6846 | 2.42 | 5145 | 1.51 |
| 11945 | 3.81 | 10244 | 3.71 | 8544 | 4.65 | 6843 | 2.42 | 5142 | 1.51 |
| 11942 | 3.95 | 10241 | 3.76 | 8540 | 4.68 | 6839 | 2.41 | 5138 | 1.51 |
| 11938 | 4.08 | 10237 | 3.77 | 8536 | 4.66 | 6835 | 2.41 | 5134 | 1.50 |
| 11934 | 4.32 | 10233 | 3.74 | 8532 | 4.68 | 6831 | 2.40 | 5130 | 1.50 |
| 11930 | 4.36 | 10229 | 3.72 | 8528 | 4.74 | 6827 | 2.40 | 5126 | 1.50 |
| 11926 | 4.05 | 10225 | 3.72 | 8524 | 4.73 | 6823 | 2.39 | 5122 | 1.50 |
| 11922 | 3.91 | 10221 | 3.74 | 8520 | 4.66 | 6819 | 2.39 | 5118 | 1.49 |
| 11918 | 3.88 | 10217 | 3.76 | 8517 | 4.67 | 6816 | 2.38 | 5115 | 1.49 |
| 11915 | 3.81 | 10214 | 3.75 | 8513 | 4.77 | 6812 | 2.38 | 5111 | 1.49 |
| 11911 | 3.74 | 10210 | 3.71 | 8509 | 4.82 | 6808 | 2.37 | 5107 | 1.49 |
| 11907 | 3.78 | 10206 | 3.68 | 8505 | 4.80 | 6804 | 2.36 | 5103 | 1.49 |
| 11903 | 3.96 | 10202 | 3.67 | 8501 | 4.72 | 6800 | 2.36 | 5099 | 1.49 |
| 11899 | 3.99 | 10198 | 3.69 | 8497 | 4.70 | 6796 | 2.35 | 5095 | 1.48 |
| 11895 | 3.96 | 10194 | 3.71 | 8493 | 4.70 | 6792 | 2.35 | 5091 | 1.48 |
| 11891 | 3.97 | 10190 | 3.72 | 8490 | 4.67 | 6789 | 2.34 | 5088 | 1.48 |
| 11888 | 3.96 | 10187 | 3.72 | 8486 | 4.62 | 6785 | 2.33 | 5084 | 1.48 |
| 11884 | 3.94 | 10183 | 3.71 | 8482 | 4.61 | 6781 | 2.33 | 5080 | 1.48 |
| 11880 | 4.00 | 10179 | 3.70 | 8478 | 4.66 | 6777 | 2.32 | 5076 | 1.47 |
| 11876 | 4.05 | 10175 | 3.70 | 8474 | 4.73 | 6773 | 2.32 | 5072 | 1.47 |
| 11872 | 4.27 | 10171 | 3.72 | 8470 | 4.69 | 6769 | 2.31 | 5068 | 1.47 |
| 11868 | 4.61 | 10167 | 3.73 | 8466 | 4.64 | 6765 | 2.31 | 5064 | 1.47 |
| 11864 | 4.42 | 10163 | 3.73 | 8463 | 4.69 | 6762 | 2.30 | 5061 | 1.46 |
| 11861 | 4.20 | 10160 | 3.70 | 8459 | 4.75 | 6758 | 2.30 | 5057 | 1.46 |
| 11857 | 4.04 | 10156 | 3.69 | 8455 | 4.74 | 6754 | 2.29 | 5053 | 1.46 |
| 11853 | 3.86 | 10152 | 3.69 | 8451 | 4.69 | 6750 | 2.29 | 5049 | 1.46 |
| 11849 | 3.81 | 10148 | 3.71 | 8447 | 4.64 | 6746 | 2.28 | 5045 | 1.46 |
| 11845 | 3.86 | 10144 | 3.73 | 8443 | 4.63 | 6742 | 2.27 | 5041 | 1.46 |
| 11841 | 3.94 | 10140 | 3.76 | 8439 | 4.65 | 6738 | 2.27 | 5037 | 1.46 |
| 11837 | 4.07 | 10136 | 3.78 | 8436 | 4.70 | 6735 | 2.26 | 5034 | 1.46 |
| 11834 | 4.08 | 10133 | 3.78 | 8432 | 4.79 | 6731 | 2.26 | 5030 | 1.46 |
| 11830 | 4.09 | 10129 | 3.77 | 8428 | 4.81 | 6727 | 2.25 | 5026 | 1.46 |
| 11826 | 4.14 | 10125 | 3.77 | 8424 | 4.81 | 6723 | 2.25 | 5022 | 1.45 |
| 11822 | 4.02 | 10121 | 3.76 | 8420 | 4.87 | 6719 | 2.24 | 5018 | 1.45 |
| 11818 | 3.97 | 10117 | 3.75 | 8416 | 5.01 | 6715 | 2.24 | 5014 | 1.45 |

TABLE 3-continued

| C1 WL, nm | C2 Abs., % | C3 WL, nm | C4 Abs., % | C5 WL, nm | C6 Abs., % | C7 WL, nm | C8 Abs., % | C9 WL, nm | C10 Abs., % |
|---|---|---|---|---|---|---|---|---|---|
| 11814 | 4.02 | 10113 | 3.74 | 8412 | 5.00 | 6711 | 2.23 | 5010 | 1.45 |
| 11810 | 4.04 | 10109 | 3.73 | 8409 | 4.90 | 6708 | 2.23 | 5007 | 1.45 |
| 11807 | 4.02 | 10106 | 3.74 | 8405 | 4.80 | 6704 | 2.22 | 5003 | 1.45 |
| 11803 | 4.07 | 10102 | 3.77 | 8401 | 4.75 | 6700 | 2.22 | 4999 | 1.46 |
| 11799 | 4.07 | 10098 | 3.79 | 8397 | 4.75 | 6696 | 2.21 | 4995 | 1.46 |
| 11795 | 4.06 | 10094 | 3.78 | 8393 | 4.78 | 6692 | 2.21 | 4991 | 1.46 |
| 11791 | 4.20 | 10090 | 3.75 | 8389 | 4.83 | 6688 | 2.20 | 4987 | 1.46 |
| 11787 | 4.39 | 10086 | 3.74 | 8385 | 4.84 | 6684 | 2.20 | 4983 | 1.46 |
| 11783 | 4.40 | 10082 | 3.75 | 8382 | 4.82 | 6681 | 2.19 | 4980 | 1.46 |
| 11780 | 4.56 | 10079 | 3.76 | 8378 | 4.78 | 6677 | 2.19 | 4976 | 1.45 |
| 11776 | 4.47 | 10075 | 3.74 | 8374 | 4.79 | 6673 | 2.18 | 4972 | 1.45 |
| 11772 | 4.35 | 10071 | 3.72 | 8370 | 4.85 | 6669 | 2.18 | 4968 | 1.45 |
| 11768 | 4.22 | 10067 | 3.70 | 8366 | 4.83 | 6665 | 2.17 | 4964 | 1.44 |
| 11764 | 4.20 | 10063 | 3.72 | 8362 | 4.85 | 6661 | 2.17 | 4960 | 1.44 |
| 11760 | 4.23 | 10059 | 3.75 | 8358 | 4.93 | 6657 | 2.16 | 4956 | 1.43 |
| 11756 | 4.30 | 10055 | 3.76 | 8355 | 4.96 | 6654 | 2.16 | 4953 | 1.43 |
| 11753 | 4.19 | 10052 | 3.74 | 8351 | 4.83 | 6650 | 2.15 | 4949 | 1.42 |
| 11749 | 4.19 | 10048 | 3.74 | 8347 | 4.74 | 6646 | 2.15 | 4945 | 1.42 |
| 11745 | 4.33 | 10044 | 3.77 | 8343 | 4.69 | 6642 | 2.14 | 4941 | 1.41 |
| 11741 | 4.18 | 10040 | 3.77 | 8339 | 4.62 | 6638 | 2.14 | 4937 | 1.41 |
| 11737 | 4.32 | 10036 | 3.74 | 8335 | 4.57 | 6634 | 2.13 | 4933 | 1.40 |
| 11733 | 4.55 | 10032 | 3.72 | 8331 | 4.55 | 6630 | 2.13 | 4929 | 1.40 |
| 11729 | 4.73 | 10028 | 3.72 | 8328 | 4.55 | 6627 | 2.12 | 4926 | 1.39 |
| 11726 | 4.57 | 10025 | 3.74 | 8324 | 4.60 | 6623 | 2.12 | 4922 | 1.39 |
| 11722 | 4.27 | 10021 | 3.78 | 8320 | 4.67 | 6619 | 2.11 | 4918 | 1.38 |
| 11718 | 4.10 | 10017 | 3.79 | 8316 | 4.69 | 6615 | 2.11 | 4914 | 1.38 |
| 11714 | 3.95 | 10013 | 3.75 | 8312 | 4.68 | 6611 | 2.10 | 4910 | 1.37 |
| 11710 | 3.89 | 10009 | 3.73 | 8308 | 4.69 | 6607 | 2.10 | 4906 | 1.37 |
| 11706 | 3.95 | 10005 | 3.75 | 8304 | 4.78 | 6603 | 2.10 | 4902 | 1.37 |
| 11702 | 4.28 | 10002 | 3.78 | 8301 | 4.87 | 6600 | 2.09 | 4899 | 1.37 |
| 11699 | 4.64 | 9998 | 3.77 | 8297 | 4.83 | 6596 | 2.09 | 4895 | 1.36 |
| 11695 | 4.43 | 9994 | 3.76 | 8293 | 4.67 | 6592 | 2.08 | 4891 | 1.36 |
| 11691 | 4.72 | 9990 | 3.74 | 8289 | 4.58 | 6588 | 2.08 | 4887 | 1.36 |
| 11687 | 4.44 | 9986 | 3.73 | 8285 | 4.60 | 6584 | 2.07 | 4883 | 1.35 |
| 11683 | 4.25 | 9982 | 3.73 | 8281 | 4.70 | 6580 | 2.07 | 4879 | 1.35 |
| 11679 | 4.11 | 9978 | 3.73 | 8277 | 4.79 | 6576 | 2.07 | 4875 | 1.35 |
| 11675 | 4.09 | 9975 | 3.73 | 8274 | 4.77 | 6573 | 2.06 | 4872 | 1.35 |
| 11672 | 4.37 | 9971 | 3.74 | 8270 | 4.67 | 6569 | 2.06 | 4868 | 1.34 |
| 11668 | 4.27 | 9967 | 3.76 | 8266 | 4.60 | 6565 | 2.05 | 4864 | 1.34 |
| 11664 | 4.00 | 9963 | 3.78 | 8262 | 4.61 | 6561 | 2.05 | 4860 | 1.33 |
| 11660 | 3.93 | 9959 | 3.78 | 8258 | 4.69 | 6557 | 2.04 | 4856 | 1.33 |
| 11656 | 4.02 | 9955 | 3.75 | 8254 | 4.68 | 6553 | 2.04 | 4852 | 1.33 |
| 11652 | 4.34 | 9951 | 3.74 | 8250 | 4.64 | 6549 | 2.04 | 4848 | 1.32 |
| 11648 | 4.36 | 9948 | 3.75 | 8247 | 4.71 | 6546 | 2.03 | 4845 | 1.32 |
| 11645 | 4.32 | 9944 | 3.78 | 8243 | 4.74 | 6542 | 2.03 | 4841 | 1.31 |
| 11641 | 4.45 | 9940 | 3.78 | 8239 | 4.65 | 6538 | 2.02 | 4837 | 1.31 |
| 11637 | 4.11 | 9936 | 3.76 | 8235 | 4.61 | 6534 | 2.02 | 4833 | 1.31 |
| 11633 | 4.08 | 9932 | 3.76 | 8231 | 4.63 | 6530 | 2.02 | 4829 | 1.30 |
| 11629 | 4.20 | 9928 | 3.76 | 8227 | 4.62 | 6526 | 2.01 | 4825 | 1.30 |
| 11625 | 4.41 | 9924 | 3.74 | 8223 | 4.55 | 6522 | 2.01 | 4821 | 1.30 |
| 11621 | 4.46 | 9921 | 3.73 | 8220 | 4.51 | 6519 | 2.00 | 4818 | 1.30 |
| 11618 | 4.15 | 9917 | 3.74 | 8216 | 4.55 | 6515 | 2.00 | 4814 | 1.30 |
| 11614 | 4.07 | 9913 | 3.76 | 8212 | 4.60 | 6511 | 2.00 | 4810 | 1.30 |
| 11610 | 4.15 | 9909 | 3.78 | 8208 | 4.58 | 6507 | 1.99 | 4806 | 1.29 |
| 11606 | 4.37 | 9905 | 3.81 | 8204 | 4.52 | 6503 | 1.99 | 4802 | 1.29 |
| 11602 | 4.36 | 9901 | 3.80 | 8200 | 4.48 | 6499 | 1.98 | 4798 | 1.29 |
| 11598 | 4.17 | 9897 | 3.76 | 8196 | 4.43 | 6495 | 1.98 | 4794 | 1.29 |
| 11594 | 4.23 | 9894 | 3.72 | 8193 | 4.39 | 6492 | 1.97 | 4791 | 1.29 |
| 11591 | 4.46 | 9890 | 3.71 | 8189 | 4.35 | 6488 | 1.97 | 4787 | 1.29 |
| 11587 | 4.48 | 9886 | 3.71 | 8185 | 4.32 | 6484 | 1.97 | 4783 | 1.29 |
| 11583 | 4.38 | 9882 | 3.72 | 8181 | 4.31 | 6480 | 1.96 | 4779 | 1.29 |
| 11579 | 4.48 | 9878 | 3.74 | 8177 | 4.31 | 6476 | 1.96 | 4775 | 1.29 |
| 11575 | 4.52 | 9874 | 3.75 | 8173 | 4.30 | 6472 | 1.95 | 4771 | 1.29 |
| 11571 | 4.28 | 9870 | 3.75 | 8169 | 4.29 | 6468 | 1.95 | 4767 | 1.29 |
| 11567 | 4.02 | 9867 | 3.75 | 8166 | 4.30 | 6465 | 1.94 | 4764 | 1.29 |
| 11564 | 3.95 | 9863 | 3.76 | 8162 | 4.30 | 6461 | 1.94 | 4760 | 1.29 |
| 11560 | 3.94 | 9859 | 3.76 | 8158 | 4.30 | 6457 | 1.93 | 4756 | 1.29 |
| 11556 | 3.90 | 9855 | 3.75 | 8154 | 4.29 | 6453 | 1.93 | 4752 | 1.29 |
| 11552 | 3.92 | 9851 | 3.73 | 8150 | 4.29 | 6449 | 1.93 | 4748 | 1.29 |
| 11548 | 4.03 | 9847 | 3.71 | 8146 | 4.30 | 6445 | 1.92 | 4744 | 1.29 |
| 11544 | 4.17 | 9843 | 3.70 | 8142 | 4.28 | 6441 | 1.92 | 4740 | 1.29 |
| 11540 | 4.25 | 9840 | 3.69 | 8139 | 4.22 | 6438 | 1.91 | 4737 | 1.29 |
| 11537 | 4.18 | 9836 | 3.69 | 8135 | 4.18 | 6434 | 1.91 | 4733 | 1.29 |
| 11533 | 4.21 | 9832 | 3.69 | 8131 | 4.18 | 6430 | 1.91 | 4729 | 1.29 |
| 11529 | 4.37 | 9828 | 3.69 | 8127 | 4.19 | 6426 | 1.90 | 4725 | 1.29 |
| 11525 | 4.25 | 9824 | 3.68 | 8123 | 4.18 | 6422 | 1.90 | 4721 | 1.29 |
| 11521 | 4.06 | 9820 | 3.68 | 8119 | 4.16 | 6418 | 1.90 | 4717 | 1.29 |

TABLE 3-continued

| C1 WL, nm | C2 Abs., % | C3 WL, nm | C4 Abs., % | C5 WL, nm | C6 Abs., % | C7 WL, nm | C8 Abs., % | C9 WL, nm | C10 Abs., % |
|---|---|---|---|---|---|---|---|---|---|
| 11517 | 3.93 | 9816 | 3.70 | 8115 | 4.13 | 6414 | 1.89 | 4713 | 1.29 |
| 11513 | 3.93 | 9813 | 3.71 | 8112 | 4.11 | 6411 | 1.89 | 4710 | 1.30 |
| 11510 | 3.97 | 9809 | 3.70 | 8108 | 4.10 | 6407 | 1.88 | 4706 | 1.30 |
| 11506 | 4.00 | 9805 | 3.70 | 8104 | 4.11 | 6403 | 1.88 | 4702 | 1.31 |
| 11502 | 4.01 | 9801 | 3.71 | 8100 | 4.12 | 6399 | 1.88 | 4698 | 1.32 |
| 11498 | 4.03 | 9797 | 3.71 | 8096 | 4.11 | 6395 | 1.87 | 4694 | 1.33 |
| 11494 | 4.08 | 9793 | 3.70 | 8092 | 4.11 | 6391 | 1.87 | 4690 | 1.35 |
| 11490 | 4.19 | 9789 | 3.69 | 8088 | 4.11 | 6387 | 1.87 | 4686 | 1.36 |
| 11486 | 4.20 | 9786 | 3.68 | 8085 | 4.10 | 6384 | 1.86 | 4683 | 1.38 |
| 11483 | 4.15 | 9782 | 3.68 | 8081 | 4.08 | 6380 | 1.86 | 4679 | 1.41 |
| 11479 | 3.97 | 9778 | 3.69 | 8077 | 4.05 | 6376 | 1.86 | 4675 | 1.44 |
| 11475 | 4.05 | 9774 | 3.70 | 8073 | 4.05 | 6372 | 1.85 | 4671 | 1.46 |
| 11471 | 4.35 | 9770 | 3.69 | 8069 | 4.05 | 6368 | 1.85 | 4667 | 1.48 |
| 11467 | 4.31 | 9766 | 3.67 | 8065 | 4.05 | 6364 | 1.85 | 4663 | 1.50 |
| 11463 | 4.33 | 9762 | 3.67 | 8061 | 4.04 | 6360 | 1.84 | 4659 | 1.51 |
| 11459 | 4.36 | 9759 | 3.68 | 8058 | 4.02 | 6357 | 1.84 | 4656 | 1.53 |
| 11456 | 4.23 | 9755 | 3.69 | 8054 | 3.99 | 6353 | 1.84 | 4652 | 1.54 |
| 11452 | 4.12 | 9751 | 3.69 | 8050 | 3.99 | 6349 | 1.83 | 4648 | 1.56 |
| 11448 | 3.97 | 9747 | 3.70 | 8046 | 4.00 | 6345 | 1.83 | 4644 | 1.57 |
| 11444 | 3.94 | 9743 | 3.72 | 8042 | 4.01 | 6341 | 1.83 | 4640 | 1.59 |
| 11440 | 3.95 | 9739 | 3.72 | 8038 | 3.99 | 6337 | 1.82 | 4636 | 1.60 |
| 11436 | 3.94 | 9735 | 3.71 | 8034 | 3.98 | 6333 | 1.82 | 4632 | 1.61 |
| 11432 | 3.99 | 9732 | 3.70 | 8031 | 3.98 | 6330 | 1.82 | 4629 | 1.63 |
| 11429 | 4.12 | 9728 | 3.70 | 8027 | 3.96 | 6326 | 1.81 | 4625 | 1.64 |
| 11425 | 4.19 | 9724 | 3.70 | 8023 | 3.94 | 6322 | 1.81 | 4621 | 1.66 |
| 11421 | 4.07 | 9720 | 3.69 | 8019 | 3.92 | 6318 | 1.81 | 4617 | 1.67 |
| 11417 | 3.97 | 9716 | 3.68 | 8015 | 3.92 | 6314 | 1.81 | 4613 | 1.69 |
| 11413 | 3.91 | 9712 | 3.67 | 8011 | 3.93 | 6310 | 1.80 | 4609 | 1.70 |
| 11409 | 3.88 | 9708 | 3.68 | 8007 | 3.93 | 6306 | 1.80 | 4605 | 1.71 |
| 11405 | 3.88 | 9705 | 3.67 | 8004 | 3.93 | 6303 | 1.80 | 4602 | 1.71 |
| 11402 | 3.91 | 9701 | 3.66 | 8000 | 3.91 | 6299 | 1.79 | 4598 | 1.71 |
| 11398 | 4.03 | 9697 | 3.66 | 7996 | 3.89 | 6295 | 1.79 | 4594 | 1.71 |
| 11394 | 4.18 | 9693 | 3.67 | 7992 | 3.87 | 6291 | 1.79 | 4590 | 1.70 |
| 11390 | 4.22 | 9689 | 3.68 | 7988 | 3.86 | 6287 | 1.78 | 4586 | 1.69 |
| 11386 | 4.10 | 9685 | 3.69 | 7984 | 3.85 | 6283 | 1.78 | 4582 | 1.68 |
| 11382 | 4.00 | 9681 | 3.71 | 7980 | 3.85 | 6279 | 1.78 | 4578 | 1.67 |
| 11378 | 4.02 | 9678 | 3.70 | 7977 | 3.86 | 6276 | 1.78 | 4575 | 1.66 |
| 11375 | 4.12 | 9674 | 3.68 | 7973 | 3.87 | 6272 | 1.77 | 4571 | 1.65 |
| 11371 | 4.11 | 9670 | 3.67 | 7969 | 3.86 | 6268 | 1.77 | 4567 | 1.64 |
| 11367 | 3.99 | 9666 | 3.66 | 7965 | 3.85 | 6264 | 1.77 | 4563 | 1.63 |
| 11363 | 3.93 | 9662 | 3.66 | 7961 | 3.83 | 6260 | 1.77 | 4559 | 1.63 |
| 11359 | 3.98 | 9658 | 3.66 | 7957 | 3.81 | 6256 | 1.76 | 4555 | 1.62 |
| 11355 | 4.07 | 9654 | 3.65 | 7953 | 3.81 | 6252 | 1.76 | 4551 | 1.63 |
| 11351 | 4.08 | 9651 | 3.64 | 7950 | 3.81 | 6249 | 1.76 | 4548 | 1.63 |
| 11348 | 4.05 | 9647 | 3.65 | 7946 | 3.81 | 6245 | 1.76 | 4544 | 1.63 |
| 11344 | 4.00 | 9643 | 3.67 | 7942 | 3.80 | 6241 | 1.75 | 4540 | 1.63 |
| 11340 | 3.94 | 9639 | 3.68 | 7938 | 3.79 | 6237 | 1.75 | 4536 | 1.64 |
| 11336 | 3.92 | 9635 | 3.68 | 7934 | 3.78 | 6233 | 1.75 | 4532 | 1.65 |
| 11332 | 4.02 | 9631 | 3.68 | 7930 | 3.77 | 6229 | 1.75 | 4528 | 1.66 |
| 11328 | 4.02 | 9627 | 3.68 | 7926 | 3.75 | 6225 | 1.74 | 4524 | 1.67 |
| 11324 | 3.99 | 9624 | 3.69 | 7923 | 3.73 | 6222 | 1.74 | 4521 | 1.68 |
| 11321 | 3.99 | 9620 | 3.69 | 7919 | 3.73 | 6218 | 1.74 | 4517 | 1.69 |
| 11317 | 3.96 | 9616 | 3.68 | 7915 | 3.73 | 6214 | 1.74 | 4513 | 1.70 |
| 11313 | 3.86 | 9612 | 3.68 | 7911 | 3.74 | 6210 | 1.74 | 4509 | 1.72 |
| 11309 | 3.80 | 9608 | 3.67 | 7907 | 3.73 | 6206 | 1.73 | 4505 | 1.73 |
| 11305 | 3.83 | 9604 | 3.67 | 7903 | 3.72 | 6202 | 1.73 | 4501 | 1.75 |
| 11301 | 3.86 | 9600 | 3.67 | 7899 | 3.71 | 6198 | 1.73 | 4497 | 1.77 |
| 11297 | 3.84 | 9597 | 3.65 | 7896 | 3.70 | 6195 | 1.73 | 4494 | 1.79 |
| 11294 | 3.85 | 9593 | 3.66 | 7892 | 3.70 | 6191 | 1.73 | 4490 | 1.81 |
| 11290 | 3.88 | 9589 | 3.69 | 7888 | 3.69 | 6187 | 1.73 | 4486 | 1.84 |
| 11286 | 3.87 | 9585 | 3.71 | 7884 | 3.68 | 6183 | 1.73 | 4482 | 1.87 |
| 11282 | 3.84 | 9581 | 3.71 | 7880 | 3.67 | 6179 | 1.73 | 4478 | 1.90 |
| 11278 | 3.82 | 9577 | 3.70 | 7876 | 3.67 | 6175 | 1.72 | 4474 | 1.94 |
| 11274 | 3.81 | 9573 | 3.70 | 7872 | 3.67 | 6171 | 1.72 | 4470 | 1.99 |
| 11270 | 3.79 | 9570 | 3.72 | 7869 | 3.67 | 6168 | 1.72 | 4467 | 2.04 |
| 11267 | 3.78 | 9566 | 3.74 | 7865 | 3.66 | 6164 | 1.72 | 4463 | 2.09 |
| 11263 | 3.78 | 9562 | 3.74 | 7861 | 3.65 | 6160 | 1.72 | 4459 | 2.16 |
| 11259 | 3.78 | 9558 | 3.72 | 7857 | 3.64 | 6156 | 1.73 | 4455 | 2.24 |
| 11255 | 3.74 | 9554 | 3.68 | 7853 | 3.63 | 6152 | 1.73 | 4451 | 2.33 |
| 11251 | 3.69 | 9550 | 3.68 | 7849 | 3.63 | 6148 | 1.73 | 4447 | 2.44 |
| 11247 | 3.70 | 9546 | 3.71 | 7845 | 3.62 | 6144 | 1.73 | 4443 | 2.57 |
| 11243 | 3.74 | 9543 | 3.75 | 7842 | 3.61 | 6141 | 1.73 | 4440 | 2.73 |
| 11240 | 3.77 | 9539 | 3.75 | 7838 | 3.60 | 6137 | 1.73 | 4436 | 2.93 |
| 11236 | 3.77 | 9535 | 3.74 | 7834 | 3.59 | 6133 | 1.73 | 4432 | 3.17 |
| 11232 | 3.77 | 9531 | 3.73 | 7830 | 3.59 | 6129 | 1.73 | 4428 | 3.44 |
| 11228 | 3.75 | 9527 | 3.74 | 7826 | 3.58 | 6125 | 1.73 | 4424 | 3.76 |
| 11224 | 3.70 | 9523 | 3.74 | 7822 | 3.58 | 6121 | 1.73 | 4420 | 4.10 |

TABLE 3-continued

| C1 WL, nm | C2 Abs., % | C3 WL, nm | C4 Abs., % | C5 WL, nm | C6 Abs., % | C7 WL, nm | C8 Abs., % | C9 WL, nm | C10 Abs., % |
|---|---|---|---|---|---|---|---|---|---|
| 11220 | 3.69 | 9519 | 3.74 | 7818 | 3.58 | 6117 | 1.73 | 4416 | 4.48 |
| 11216 | 3.70 | 9516 | 3.75 | 7815 | 3.57 | 6114 | 1.73 | 4413 | 4.84 |
| 11213 | 3.74 | 9512 | 3.74 | 7811 | 3.57 | 6110 | 1.73 | 4409 | 5.02 |
| 11209 | 3.79 | 9508 | 3.74 | 7807 | 3.56 | 6106 | 1.73 | 4405 | 5.07 |
| 11205 | 3.77 | 9504 | 3.75 | 7803 | 3.55 | 6102 | 1.73 | 4401 | 5.06 |
| 11201 | 3.72 | 9500 | 3.77 | 7799 | 3.54 | 6098 | 1.73 | 4397 | 5.03 |
| 11197 | 3.71 | 9496 | 3.76 | 7795 | 3.54 | 6094 | 1.73 | 4393 | 5.04 |
| 11193 | 3.73 | 9492 | 3.73 | 7791 | 3.53 | 6090 | 1.73 | 4389 | 5.12 |
| 11189 | 3.74 | 9489 | 3.73 | 7788 | 3.52 | 6087 | 1.73 | 4386 | 5.15 |
| 11186 | 3.68 | 9485 | 3.74 | 7784 | 3.52 | 6083 | 1.73 | 4382 | 5.08 |
| 11182 | 3.65 | 9481 | 3.74 | 7780 | 3.52 | 6079 | 1.73 | 4378 | 5.05 |
| 11178 | 3.71 | 9477 | 3.73 | 7776 | 3.51 | 6075 | 1.73 | 4374 | 5.11 |
| 11174 | 3.78 | 9473 | 3.73 | 7772 | 3.50 | 6071 | 1.73 | 4370 | 5.23 |
| 11170 | 3.79 | 9469 | 3.74 | 7768 | 3.49 | 6067 | 1.73 | 4366 | 5.43 |
| 11166 | 3.78 | 9465 | 3.76 | 7764 | 3.49 | 6063 | 1.73 | 4362 | 5.50 |
| 11162 | 3.76 | 9462 | 3.76 | 7761 | 3.48 | 6060 | 1.73 | 4359 | 5.41 |
| 11159 | 3.72 | 9458 | 3.75 | 7757 | 3.48 | 6056 | 1.74 | 4355 | 5.33 |
| 11155 | 3.69 | 9454 | 3.74 | 7753 | 3.48 | 6052 | 1.74 | 4351 | 5.23 |
| 11151 | 3.68 | 9450 | 3.73 | 7749 | 3.47 | 6048 | 1.74 | 4347 | 5.12 |
| 11147 | 3.68 | 9446 | 3.73 | 7745 | 3.46 | 6044 | 1.74 | 4343 | 5.08 |
| 11143 | 3.67 | 9442 | 3.73 | 7741 | 3.45 | 6040 | 1.75 | 4339 | 5.11 |
| 11139 | 3.67 | 9438 | 3.74 | 7737 | 3.45 | 6036 | 1.75 | 4335 | 5.18 |
| 11135 | 3.67 | 9435 | 3.75 | 7734 | 3.45 | 6033 | 1.76 | 4332 | 5.19 |
| 11132 | 3.67 | 9431 | 3.77 | 7730 | 3.44 | 6029 | 1.77 | 4328 | 5.23 |
| 11128 | 3.68 | 9427 | 3.79 | 7726 | 3.44 | 6025 | 1.78 | 4324 | 5.25 |
| 11124 | 3.68 | 9423 | 3.80 | 7722 | 3.42 | 6021 | 1.79 | 4320 | 5.22 |
| 11120 | 3.67 | 9419 | 3.80 | 7718 | 3.41 | 6017 | 1.80 | 4316 | 5.24 |
| 11116 | 3.63 | 9415 | 3.78 | 7714 | 3.40 | 6013 | 1.81 | 4312 | 5.25 |
| 11112 | 3.59 | 9411 | 3.78 | 7710 | 3.40 | 6009 | 1.82 | 4308 | 5.28 |
| 11108 | 3.57 | 9408 | 3.79 | 7707 | 3.40 | 6006 | 1.84 | 4305 | 5.36 |
| 11105 | 3.53 | 9404 | 3.80 | 7703 | 3.40 | 6002 | 1.85 | 4301 | 5.44 |
| 11101 | 3.48 | 9400 | 3.82 | 7699 | 3.39 | 5998 | 1.87 | 4297 | 5.50 |
| 11097 | 3.46 | 9396 | 3.85 | 7695 | 3.39 | 5994 | 1.89 | 4293 | 5.32 |
| 11093 | 3.46 | 9392 | 3.86 | 7691 | 3.38 | 5990 | 1.91 | 4289 | 5.23 |
| 11089 | 3.47 | 9388 | 3.86 | 7687 | 3.37 | 5986 | 1.93 | 4285 | 5.23 |
| 11085 | 3.50 | 9384 | 3.85 | 7683 | 3.37 | 5982 | 1.95 | 4281 | 5.21 |
| 11081 | 3.53 | 9381 | 3.85 | 7680 | 3.36 | 5979 | 1.97 | 4278 | 5.28 |
| 11078 | 3.53 | 9377 | 3.87 | 7676 | 3.35 | 5975 | 1.99 | 4274 | 5.28 |
| 11074 | 3.49 | 9373 | 3.90 | 7672 | 3.35 | 5971 | 2.02 | 4270 | 5.18 |
| 11070 | 3.47 | 9369 | 3.92 | 7668 | 3.35 | 5967 | 2.04 | 4266 | 5.26 |
| 11066 | 3.48 | 9365 | 3.92 | 7664 | 3.34 | 5963 | 2.06 | 4262 | 5.27 |
| 11062 | 3.49 | 9361 | 3.91 | 7660 | 3.33 | 5959 | 2.09 | 4258 | 5.29 |
| 11058 | 3.48 | 9357 | 3.92 | 7656 | 3.33 | 5955 | 2.12 | 4254 | 5.28 |
| 11054 | 3.47 | 9354 | 3.92 | 7653 | 3.32 | 5952 | 2.15 | 4251 | 5.19 |
| 11051 | 3.48 | 9350 | 3.93 | 7649 | 3.31 | 5948 | 2.18 | 4247 | 5.23 |
| 11047 | 3.48 | 9346 | 3.94 | 7645 | 3.31 | 5944 | 2.22 | 4243 | 5.30 |
| 11043 | 3.47 | 9342 | 3.96 | 7641 | 3.30 | 5940 | 2.26 | 4239 | 5.44 |
| 11039 | 3.45 | 9338 | 3.95 | 7637 | 3.30 | 5936 | 2.31 | 4235 | 5.46 |
| 11035 | 3.47 | 9334 | 3.96 | 7633 | 3.29 | 5932 | 2.38 | 4231 | 5.34 |
| 11031 | 3.51 | 9330 | 3.98 | 7629 | 3.28 | 5928 | 2.46 | 4227 | 5.28 |
| 11027 | 3.54 | 9327 | 4.01 | 7626 | 3.28 | 5925 | 2.55 | 4224 | 5.25 |
| 11024 | 3.56 | 9323 | 4.02 | 7622 | 3.28 | 5921 | 2.66 | 4220 | 5.15 |
| 11020 | 3.53 | 9319 | 4.00 | 7618 | 3.27 | 5917 | 2.77 | 4216 | 5.21 |
| 11016 | 3.48 | 9315 | 3.98 | 7614 | 3.26 | 5913 | 2.87 | 4212 | 5.32 |
| 11012 | 3.46 | 9311 | 3.98 | 7610 | 3.26 | 5909 | 2.96 | 4208 | 5.17 |
| 11008 | 3.48 | 9307 | 4.00 | 7606 | 3.25 | 5905 | 3.01 | 4204 | 5.07 |
| 11004 | 3.49 | 9303 | 4.02 | 7602 | 3.25 | 5901 | 3.03 | 4200 | 5.06 |
| 11000 | 3.48 | 9300 | 4.03 | 7599 | 3.24 | 5898 | 3.04 | 4197 | 5.21 |
| 10997 | 3.46 | 9296 | 4.08 | 7595 | 3.24 | 5894 | 3.06 | 4193 | 5.35 |
| 10993 | 3.47 | 9292 | 4.16 | 7591 | 3.23 | 5890 | 3.09 | 4189 | 5.37 |
| 10989 | 3.49 | 9288 | 4.20 | 7587 | 3.23 | 5886 | 3.14 | 4185 | 5.54 |
| 10985 | 3.50 | 9284 | 4.15 | 7583 | 3.22 | 5882 | 3.22 | 4181 | 5.27 |
| 10981 | 3.50 | 9280 | 4.08 | 7579 | 3.22 | 5878 | 3.31 | 4177 | 5.09 |
| 10977 | 3.48 | 9276 | 4.05 | 7575 | 3.21 | 5874 | 3.41 | 4173 | 5.11 |
| 10973 | 3.46 | 9273 | 4.07 | 7572 | 3.20 | 5871 | 3.49 | 4170 | 5.27 |
| 10970 | 3.47 | 9269 | 4.10 | 7568 | 3.19 | 5867 | 3.54 | 4166 | 5.20 |
| 10966 | 3.50 | 9265 | 4.12 | 7564 | 3.19 | 5863 | 3.55 | 4162 | 5.10 |
| 10962 | 3.51 | 9261 | 4.12 | 7560 | 3.18 | 5859 | 3.54 | 4158 | 5.08 |
| 10958 | 3.51 | 9257 | 4.11 | 7556 | 3.18 | 5855 | 3.51 | 4154 | 5.01 |
| 10954 | 3.52 | 9253 | 4.10 | 7552 | 3.18 | 5851 | 3.49 | 4150 | 5.08 |
| 10950 | 3.54 | 9249 | 4.14 | 7548 | 3.18 | 5847 | 3.48 | 4146 | 5.32 |
| 10946 | 3.57 | 9246 | 4.21 | 7545 | 3.17 | 5844 | 3.49 | 4143 | 5.52 |
| 10943 | 3.57 | 9242 | 4.24 | 7541 | 3.16 | 5840 | 3.51 | 4139 | 5.39 |
| 10939 | 3.53 | 9238 | 4.25 | 7537 | 3.16 | 5836 | 3.54 | 4135 | 5.16 |
| 10935 | 3.50 | 9234 | 4.28 | 7533 | 3.15 | 5832 | 3.59 | 4131 | 5.14 |
| 10931 | 3.51 | 9230 | 4.31 | 7529 | 3.15 | 5828 | 3.65 | 4127 | 5.17 |
| 10927 | 3.54 | 9226 | 4.33 | 7525 | 3.14 | 5824 | 3.72 | 4123 | 5.14 |

TABLE 3-continued

| C1 WL, nm | C2 Abs., % | C3 WL, nm | C4 Abs., % | C5 WL, nm | C6 Abs., % | C7 WL, nm | C8 Abs., % | C9 WL, nm | C10 Abs., % |
|---|---|---|---|---|---|---|---|---|---|
| 10923 | 3.56 | 9222 | 4.34 | 7521 | 3.13 | 5820 | 3.80 | 4119 | 5.12 |
| 10919 | 3.58 | 9219 | 4.33 | 7518 | 3.13 | 5817 | 3.87 | 4116 | 5.25 |
| 10916 | 3.58 | 9215 | 4.29 | 7514 | 3.12 | 5813 | 3.94 | 4112 | 5.28 |
| 10912 | 3.58 | 9211 | 4.27 | 7510 | 3.12 | 5809 | 4.01 | 4108 | 5.05 |
| 10908 | 3.59 | 9207 | 4.31 | 7506 | 3.12 | 5805 | 4.05 | 4104 | 4.93 |
| 10904 | 3.59 | 9203 | 4.33 | 7502 | 3.11 | 5801 | 4.07 | 4100 | 5.01 |
| 10900 | 3.56 | 9199 | 4.28 | 7498 | 3.10 | 5797 | 4.08 | 4096 | 5.22 |
| 10896 | 3.55 | 9195 | 4.23 | 7494 | 3.10 | 5793 | 4.08 | 4092 | 5.28 |
| 10892 | 3.56 | 9192 | 4.24 | 7491 | 3.09 | 5790 | 4.06 | 4089 | 5.16 |
| 10889 | 3.58 | 9188 | 4.27 | 7487 | 3.09 | 5786 | 4.03 | 4085 | 5.01 |
| 10885 | 3.58 | 9184 | 4.27 | 7483 | 3.08 | 5782 | 3.98 | 4081 | 5.00 |
| 10881 | 3.59 | 9180 | 4.25 | 7479 | 3.08 | 5778 | 3.91 | 4077 | 5.05 |
| 10877 | 3.59 | 9176 | 4.25 | 7475 | 3.07 | 5774 | 3.83 | 4073 | 5.04 |
| 10873 | 3.59 | 9172 | 4.29 | 7471 | 3.07 | 5770 | 3.74 | 4069 | 4.98 |
| 10869 | 3.60 | 9168 | 4.33 | 7467 | 3.06 | 5766 | 3.64 | 4065 | 4.90 |
| 10865 | 3.61 | 9165 | 4.35 | 7464 | 3.06 | 5763 | 3.53 | 4062 | 4.91 |
| 10862 | 3.62 | 9161 | 4.36 | 7460 | 3.05 | 5759 | 3.43 | 4058 | 5.04 |
| 10858 | 3.61 | 9157 | 4.34 | 7456 | 3.05 | 5755 | 3.34 | 4054 | 5.21 |
| 10854 | 3.59 | 9153 | 4.31 | 7452 | 3.04 | 5751 | 3.25 | 4050 | 5.13 |
| 10850 | 3.56 | 9149 | 4.28 | 7448 | 3.04 | 5747 | 3.18 | 4046 | 4.98 |
| 10846 | 3.55 | 9145 | 4.23 | 7444 | 3.04 | 5743 | 3.11 | 4042 | 4.95 |
| 10842 | 3.57 | 9141 | 4.19 | 7440 | 3.03 | 5739 | 3.06 | 4038 | 5.02 |
| 10838 | 3.62 | 9138 | 4.18 | 7437 | 3.03 | 5736 | 3.02 | 4035 | 4.99 |
| 10835 | 3.67 | 9134 | 4.22 | 7433 | 3.02 | 5732 | 2.99 | 4031 | 4.92 |
| 10831 | 3.70 | 9130 | 4.25 | 7429 | 3.02 | 5728 | 2.99 | 4027 | 4.93 |
| 10827 | 3.70 | 9126 | 4.27 | 7425 | 3.01 | 5724 | 2.99 | 4023 | 5.07 |
| 10823 | 3.67 | 9122 | 4.29 | 7421 | 3.01 | 5720 | 3.00 | 4019 | 5.12 |
| 10819 | 3.62 | 9118 | 4.29 | 7417 | 3.00 | 5716 | 3.00 | 4015 | 4.89 |
| 10815 | 3.57 | 9114 | 4.26 | 7413 | 3.00 | 5712 | 3.01 | 4011 | 4.75 |
| 10811 | 3.55 | 9111 | 4.23 | 7410 | 3.00 | 5709 | 3.03 | 4008 | 4.82 |
| 10808 | 3.58 | 9107 | 4.24 | 7406 | 3.00 | 5705 | 3.04 | 4004 | 5.01 |
| 10804 | 3.63 | 9103 | 4.27 | 7402 | 2.99 | 5701 | 3.07 | 4000 | 5.04 |
| 10800 | 3.62 | 9099 | 4.28 | 7398 | 2.99 | 5697 | 3.09 | | |
| 10796 | 3.59 | 9095 | 4.27 | 7394 | 2.99 | 5693 | 3.12 | | |
| | 1674.09 | | 1667.16 | | 1847.95 | | 1075.85 | | 1136.82 |

I claim:

1. A system for assigning aromatic content and naphthene content to a naphtha fraction of a crude oil sample, based upon analysis of the crude oil sample, the system comprising:
   a non-volatile memory device that stores calculation modules and crude oil sample analysis data derived from Fourier transform near infrared spectroscopy;
   a processor coupled to the memory;
   a first calculation module that calculates and assigns an index of the crude oil sample based on a summation of absorbances for peaks detected over a predetermined wavenumber range; and
   a second calculation module that calculates and assigns paraffin content, aromatic content and naphthene content to the naphtha fraction based on the index of the crude oil sample and a density of the crude oil sample according to the equations:

paraffin content=$KPa+KPb*DEN+KPc*DEN^2+KPd*DEN^3+KPe*I+KPf*I^2+KPg*I^3+KPh*DEN*I$;

aromatic content=$KAa+KAb*DEN+KAc*DEN^2+KAd*DEN^3+KAe*I+KAf*I^2+KAg*I^3+KAh*DEN*I$; and naphthene content=100−paraffin content aromatic content;

where KPa through KPh and KAa through KAh are constants,
   DEN=density of crude oil at 15° C., and
   I=the index of the crude oil sample;
   wherein the non-volatile memory device including a computer readable program code embodied therein as said calculation modules, the computer readable program code adapted to be executed by the processor coupled to the non-volatile memory device.

2. The system as in claim 1, further comprising
   a third calculation module that calculates and assigns a total liquid products yield based on the assigned aromatic content and naphthene content;
   a fourth calculation module that calculates and assigns raw product yield to each of methane, ethane, propane, butane and gasoline based on the assigned total liquid products yield;
   a fifth calculation module that calculates and assigns a raw product yield of hydrogen based on the assigned total liquid product yield; and
   a sixth calculation module that calculates and assigns values to each of hydrogen, methane, ethane, propane, butane and gasoline based on the raw product yields of each of hydrogen, methane, ethane, propane, butane and gasoline and a unit value of each product.

3. The system as in claim 1, wherein the crude oil analysis data is derived from Fourier transform near infrared spectroscopy, and wherein the index is a near infrared spectroscopy index (NIRA) of the crude oil analysis data is determined according to the equation $$NIRA = \sum_i (Absorbance_{(i)}/10,000,$$

, wherein absorbance is absorbance value of the crude oil solution for peaks detected over a predetermined wavenumber range i.

4. A method for operating a computer to assign aromatic content and naphthene content to a naphtha fraction of a crude oil sample, based upon analysis of the crude oil sample, the method comprising:
receiving, by a non-volatile memory, crude oil sample analysis data derived from Fourier transform near infrared spectroscopy;
calculating and assigning an index to the crude oil sample based on a summation of absorbances for peaks detected over a predetermined wavenumber range; and
calculating and assigning paraffin content, aromatic content and naphthene content to the naphtha fraction of the crude oil sample based on the index and the density of the crude oil sample according to the equations:

paraffin content=$KPa+KPb*DEN+KPc*DEN^2+KPd*DEN^3+Kpe*I+KPf*I^2+KPg*I^3+KPh*DEN*I$;

aromatic content=$Kaa+Kab*DEN+Kac*DEN^2+Kad*DEN^3+Kae*I+Kaf*I^2+Kag*I^3+Kah*DEN*I$; and naphthene content=100−paraffin content−aromatic content;

where Kpa through KPh and Kaa through Kah are constants,
DEN=Density of crude oil at 15° C., and
I=the index of the crude oil sample.

5. The method as in claim 4, further comprising
calculating and assigning a total liquid products yield based on the aromatic content and naphthene content;
calculating and assigning a raw product yield to each of methane, ethane, propane, butane and gasoline based on the assigned total liquid products yield;
calculating and assigning a raw product yield of hydrogen based on the assigned total liquid product yield; and
calculating and assigning a value to each of hydrogen, methane, ethane, propane, butane and gasoline based on the raw product yields of each of hydrogen, methane, ethane, propane, butane and gasoline and a unit value of each product.

6. The method as in claim 4, wherein the crude oil analysis data is derived from Fourier transform near infrared spectroscopy, and wherein the index is a near infrared spectroscopy index (NIRA) of the crude oil analysis data is determined according to the equation $$NIRA = \sum_i (\text{Absorbance}_{(i)}/10,000,$$

, wherein absorbance is absorbance value of the crude oil solution for peaks detected over a predetermined wavenumber range i.

7. A system for assigning aromatic content and naphthene content to a naphtha fraction of a crude oil sample, based upon analysis of the crude oil sample, the system comprising:
a non-volatile memory device that stores calculation modules and crude oil sample analysis data derived from Fourier transform near infrared spectroscopy;
a processor coupled to the memory;
a first calculation module that calculates and assigns an index of the crude oil sample based on the crude oil analysis data, wherein the index is a near infrared spectroscopy index (NIRA) of the crude oil sample that is determined according to the equation $$NIRA = \sum_i (\text{Absorbance}_{(i)}/10,000,$$

, wherein absorbance is absorbance value of the crude oil solution for peaks detected over a predetermined wavenumber range i; and
a second calculation module that calculates and assigns paraffin content, aromatic content and naphthene content to the naphtha fraction based on the NIRA of the crude oil sample and a density of the crude oil sample;
the non-volatile memory device including a computer readable program code embodied therein as said calculation modules, the computer readable program code adapted to be executed by the processor coupled to the non-volatile memory device.

8. The system as in claim 7, wherein the paraffin, aromatic and naphthene contents are calculated and assigned according to the equations:

paraffin content=$KPa+KPb*DEN+KPc*DEN^2+KPd*DEN^3+KPe*I+KPf*I^2+KPg*I^3+KPh*DEN*I$;

aromatic content=$KAa+KAb*DEN+KAc*DEN^2+KAd*DEN^3+KAe*I+KAf*I^2+KAg*I^3+KAh*DEN*I$; and naphthene content=100−paraffin content−aromatic content;

where KPa through KPh and KAa through KAh are constants,
DEN=density of crude oil at 15° C., and
I=the NIRA of the crude oil sample.

9. The system as in claim 7, further comprising
a third calculation module that calculates and assigns a total liquid products yield based on the assigned aromatic content and naphthene content;
a fourth calculation module that calculates and assigns raw product yield to each of methane, ethane, propane, butane and gasoline based on the assigned total liquid products yield;
a fifth calculation module that calculates and assigns a raw product yield of hydrogen based on the assigned total liquid product yield; and
a sixth calculation module that calculates and assigns values to each of hydrogen, methane, ethane, propane, butane and gasoline based on the raw product yields of each of hydrogen, methane, ethane, propane, butane and gasoline and a unit value of each product.

10. A method for operating a computer to assign aromatic content and naphthene content to a naphtha fraction of a crude oil sample, based upon analysis of the crude oil sample, the method comprising:
receiving, by a non-volatile memory, crude oil sample analysis data derived from Fourier transform near infrared spectroscopy;
calculating and assigning an index to the crude oil sample based on the crude oil analysis data, wherein the index is a near infrared spectroscopy index (NIRA) of the crude oil sample data is determined according to the equation $$NIRA = \sum_i (\text{Absorbance}_{(i)} / 10{,}000),$$

, wherein absorbance is absorbance value of the crude oil solution for peaks detected over a predetermined wavenumber range i; and calculating and assigning paraffin content, aromatic content and naphthene content to the naphtha fraction of the crude oil sample based on the NIRA and the density of the crude oil sample.

11. The method as in claim 10, wherein the paraffin, aromatic and naphthene contents are calculated and assigned according to the equations:

paraffin Content=$KPa+KPb*DEN+KPc*DEN^2+KPd*DEN^3+KPe*I+KPf*I^2+KPg*I^3+KPh*DEN*I$;

aromatic Content=$KAa+KAb*DEN+KAc*DEN^2+KAd*DEN^3+KAe*I+KAf*I^2+KAg*I^3+KAh*DEN*I$; and naphthene Content=100−Paraffin Content−Aromatic Content;

where KPa through KPh and KAa through KAh are constants,

DEN=Density of crude oil at 15° C., and

I=the NIRA of the crude oil sample.

12. The method as in claim 11, further comprising calculating and assigning a total liquid products yield based on the aromatic content and naphthene content;

calculating and assigning a raw product yield to each of methane, ethane, propane, butane and gasoline based on the assigned total liquid products yield;

calculating and assigning a raw product yield of hydrogen based on the assigned total liquid product yield; and calculating and assigning a value to each of hydrogen, methane, ethane, propane, butane and gasoline based on the raw product yields of each of hydrogen, methane, ethane, propane, butane and gasoline and a unit value of each product.

\* \* \* \* \*